(12) United States Patent
Wang et al.

(10) Patent No.: US 7,279,158 B2
(45) Date of Patent: Oct. 9, 2007

(54) METHODS FOR THE TREATMENT OF INFLAMMATORY JOINT DISEASE

(75) Inventors: Yi Wang, Orange, CT (US); Louis Matis, Southport, CT (US)

(73) Assignee: Alexion Pharmaceuticals, Inc., Cheshire, CT (US)

(*) Notice: Subject to any disclaimer, the term of this patent is extended or adjusted under 35 U.S.C. 154(b) by 0 days.

(21) Appl. No.: 11/029,017

(22) Filed: Jan. 5, 2005

(65) Prior Publication Data

US 2005/0226870 A1 Oct. 13, 2005

Related U.S. Application Data

(63) Continuation of application No. 08/867,612, filed on Jun. 2, 1997, now abandoned, which is a continuation of application No. 08/311,489, filed on Sep. 23, 1994, now abandoned.

(51) Int. Cl.
*A61K 39/395* (2006.01)
*C07K 16/00* (2006.01)
*C12Q 1/00* (2006.01)
*G01N 33/53* (2006.01)

(52) U.S. Cl. .............. 424/130.1; 424/141.1; 424/145.1; 424/152.1; 424/158.1; 424/172.1; 424/810; 514/825; 514/885; 530/388.25; 530/389.3; 530/868; 435/4; 435/7.1; 435/7.2; 435/7.24; 435/29; 436/821

(58) Field of Classification Search .............. 424/130.1, 424/141.1, 145.1, 152.1, 158.1, 172.1, 810; 514/825, 885; 530/388.25, 389.3, 868; 435/4, 435/7.1, 7.2, 7.24; 436/821

See application file for complete search history.

(56) References Cited

U.S. PATENT DOCUMENTS

| 5,135,916 | A | | 8/1992 | Sims et al. |
|---|---|---|---|---|
| 5,173,499 | A | | 12/1992 | Sindelar et al. |
| 5,635,178 | A | * | 6/1997 | Sims et al. .............. 424/145.1 |
| 5,853,722 | A | | 12/1998 | Rollins et al. |
| 6,074,642 | A | | 6/2000 | Wang et al. |

FOREIGN PATENT DOCUMENTS

| EP | 0245993 | 11/1987 |
|---|---|---|
| WO | WO-94/03603 | 2/1994 |
| WO | WO-94/26786 | 11/1994 |
| WO | WO-95/23856 | 9/1995 |
| WO | WO-95/25540 | 9/1995 |
| WO | WO-95/29697 | 11/1995 |

OTHER PUBLICATIONS

Güssow, D et al. Meth. Enzymology [1991] 203:99-117.*
Abbnik et al "Relative contribution of contact and complement activation to inflammatory reactions in arthritic joints." Annu. Rheumat. Dis, 51:1123-1128. (1992).
Anderson, R. et al. "Immunological assessment of patients with rheumatoid arthritis—evaluation of the effects of propranolol." S.A. Medical Journal, 666-669. (1981).
Anderson et al. Letter to the editor. Immunogenetics, 35:71-72.
Anderson and Holmdahl. "Analysis of type II collagen-reactive T cells in the mouse—I. Different regulation of autoreactive vs. non-autoreactive anti-type II collagen T cells in the DBA/1 mouse." Eur. J. Immunol., 20:1061-1066. (1990).
Andersson et al. Letter to the Editor. Immunogenet, 35:71-72. (1992).
Andersson et al. "T-cell receptor Vβ haplotype and complement component C5 play no significant role for the resistance to collagen-induced arthritis in the SWR mouse." Immunol., 73:191-196. (1991).
Auda et al. "Measurement of complement activation products in patients with chronic rheumatic diseases." Rheumat. Int., 10:185-189. (1990).
Banapour et al. "The AIDS-associated retrovirus is not sensitive to lysis or inactivation by human serum" Virology 152:268-271. (1986).
Banerjee et al. "Influence of complement C5 and Vβ T cell receptor mutations on susceptibility to collagen-induced arthritis in mice." J. Immunol, 142:2237-2243. (1989).
Banerjee et al. "Possible role of Vβ T cell receptor genes in susceptibility to collagen-induced arthritis in mice." J. Exp. Med., 167:832-839. (1988).
Barbacid et al. "Humans have antibodies capable of recognizing oncoviral gllycoproteins: Demonstration that these antibodies are formed in response to cellular modification of glycoproteins rather than as consequence of exposure virus." Proc. Natl. Acad. Sci. USA 77:1617-1621. (1980).
Bartholomew et al. "Lysis of oncornaviruses by human serum." J. Exp. Med, 147:844-853. (1978).
Bartholomew et al. "Mechanism of antibody-independent activation of the first component of complement (C1) on retrovirus membranes." Biochem. 19:2847-2853. (1980).
Brahn and Trentham. "Experimental synovitis induced by collagen-specific T cell lines." Cell Immunol., 118:491-503. (1989).
Brenner, M. "Genetic marketing and manipulation of hematopoietic progenitor cells using retroviral vectors." Immunmethods 5:204-210. (1994).
Brodeur et al. "Synovial fluid levels of complement SC5b-9 and fragment Bb are elevated in patients with rheumatoid arthritis." Arthr Rheumat, 34:1531-1537. (1990).
Chiocchia et al. "T cell regulation of collagen-induced arthritis in mice." J. Immunol., 145:519-525. (1990).

(Continued)

*Primary Examiner*—Christina Chan
*Assistant Examiner*—F. Pierre VanderVegt
(74) *Attorney, Agent, or Firm*—Ropes & Gray LLP

(57) ABSTRACT

The use of compounds that block complement component C5 or its active fragments C5a and/or C5b (such compounds collectively referred to as "C5 blockers") to treat established joint inflammation (arthritis) is disclosed. Administration of such C5 blockers has been found to: 1) arrest and/or reduce inflammation in joints which are already inflamed, and 2) inhibit the spread of inflammation to unaffected joints.

17 Claims, 14 Drawing Sheets

OTHER PUBLICATIONS

Chiocchia et al. "Therapy against murine collagen-induced arthritis with T cell receptor Vβ-specific antibodies." Eur J. Immunol., 21:2899-2905. (1991).

Cooper et al. "Lysis of RNA tumor viruses by human serum: Direct antibody-independent triggering of the classical complement pathway." J. Exp Med, 144:970-984. (1976).

Corvetta et al. "Terminal complement complex in synovial tissue from patients affected by rheumatoid arthritis, osteoarthritis and acute joint trauma." Clin. Exp. Rheumat., 10:433-438. (1992).

David, "Role for T-cell receptor Vβ genes in collagen induced-arthritis." Immunogenet, 35:69-70. (1992).

De Clerk et al. "Humoral immunity and composition of immune complexes in patients with rheumatoid arthritis, with special reference to IgE-containing immune complexes." Clin Exp. Rheumat., 7:485-492. (1989).

Durie et al. "Prevention of collagen-induced arthritis with an antibody to gp39, the ligand for CD40." Science, 261:1328-1330. (1993).

Fava et al. "Critical role of peripheral blood phagocytes and the involvement of complement in tumour necrosis factor enhancement of passive collagen-arthritis." Clin. Exp. Immunol., 94:261-266. (1993).

Feldmann et al. "Cytokine assays: Role in evaluation of the pathogenesis of autoimmunity." Immunol. Rev., 119:105-123. (1991).

Feldmann et al. "Cytokine production in the rheumatoid joint: Implications for treatment." Anna Rheumat. Dis., 49:480-486. (1990).

Firestein et al. "Gene expression (collagenase, tissue inhibitor of metalloproteinases, complement, and HLA-DR) in rheumatoid arthritis and osteoarthritis synovium." Arthr Rheumat., 34:1094-1105. (1991).

Fong et al. "Cytokine concentrations in the synovial fluid and plasma of rheumatoid arthritis patients: Correlation with bony erosions." Clin. Exp. Rheumat., 12:55-58. (1994).

Frei et al. "Generation of a monoclonal antibody to mouse C5 application in an ELISA asay for detection of anti-C5 antibodies." Mol. Cell Probes, 1:141-149. (1987).

Galili et al. "Evolution and pathophsiology of the human natural anti-a-galactosyl IgG (Anti-Gal) antibody." Springer Semin Immunopathol, 15:155-171. (1993).

Geyer et al. "Major oligosaccharides in the glycoprotein of friend murine leukemia virus: structure elucidation by one—and two dimensional proton nuclear magnetic resonance and methylation analysis." Biochemistry 23:5628-5637. (1984).

Goldschmidt and Holmdahl, "Anti-T cell receptor antibody treatment of rats with established autologous collagen-induced arthritis: Suppression of arthritis without reduction of anti-type II collagen autoantibody levels." Eur. J. Immunol. 21:1327-1330. (1991).

Goldschmidt et al. "Invivo elimination of T cells expressing specific T-cell receptor Vβ chains in mice susceptible to collagen-induced arthritis." Immunol., 69:508-514. (1990).

Hamadeh et al. "Human Natural anti-gal IgG regulates alternative complement pathway activation on bacterial surfaces." J. Clin. Invest., 89:1223-1235. (1992).

Haqqi et al. "Identification of T-cell receptor Vβ deletion mutant mouse strain AU/ssJ (H-2$^q$) which is resistant to collagen-induced arthritis." Immunogenet, 29:180-185. (1989).

Harigai et al. "Monocyte chemoattractant protein-1 (MCP-1) in inflammatory joint diseases and its involvement in the cytokine network of rheumatoid synvium." Clin. Immunol. Immunopath, 69:83-91. (1993).

Heinz et al. "Common epitopes in Clq and collagen type II." Mol. Immunol., 26:163-169. (1989).

Holmdahl et al. "Arthritis in DBA/1 mice induced with passively transferred type II collagen immune serum." Scand. J. Immunol., 31:147-157. (1990).

Holmdahl et al. "Collagen induced arthritis: an experimental model for rheumatoid arthritis with involvement of both DTH and immune complex mediated mechanisms." Clin. Exp. Rheumat., 7/S-3:57-55. (1989).

Holmdahl et al. "T lymphocytes in collagen II-induced arthritis in mice." Scand. J. Immunol, 22:295-306. (1985).

Hom et al., "Effects of various anti-T cell receptor antibodies on the development of type II collagen-induced arthritis in mice." Immunol. Invest. 22:257-265. (1993).

Hom et al. "Interleukin-1 enhances the development of type II collagen-induced arthritis only in susceptible and not in resistant mice." Clin. Immunol. Immunopath, 62:56-65. (1992).

Hom et al. "The progression of the inflammation in established collagen-induced arthritis can be altered by treatments with immunological or pharmacological agents which inhibit T cell activities." Eur. J. Immunol., 18:881-888. (1988).

Hong et al. "An anticomplementary agent, K-76 monocarboxylic acid: Its site and mechanism of inhibition of the complement activation cascade." J. Immunol., 122:2418-2423. (1979).

Hoshino et al. "Human T-cell leukemia virus is not lysed by human serum." Nature, 310:324-325. (1984).

Isaacs et al. "Vaccinia virus complement-control protein prevents antibody-dependent complement-enhanced neutralization of infectivity and contributes to virulence." Proc. Natl. Acad. Sci., USA, 89:628-632. (1992).

Jazin. "Immune mechanisms in osteoarthritis." Sem. Arthr. Rheumat., 18:86-90. (1989).

Jose et al. "Measurement of the chemotactic complement fragment C5a in rheumatoid synovial fluids by radioimmunoassay: Role of C5a in the acute inflammatory phase." Anna. Rheumat. Dis., 49:747-752. (1990).

Joziasses et al. "Vobine al-3 galactosyltransferase: Isolation and characterization of a cDNA clone." J. Biol. Chem., 264:14290-14297. (1989).

Kahle et al. "Determination of cytokines in synovial fluids: Correlation with diagnosis and histomorphological characteristics of synovial tissue." Anna. Rheumat. Dis., 51:731-734. (1992).

Kakimoto et al. "Isolation of T cell line capable of protecting mice against collagen-induced arthritis." J. Immunol., 140:78-83. (1988).

Koch et al. "Epithelial neutrophil activating peptide-78: A novel chemotactic cytokine for neutrophils in arthritis." J. Clin. Invest., 94:1012-1018. (1994).

Kohn et al. "Retroviral-mediated gene transfer into mammalian cells." Blood Cells, 13:285-298. (1987).

Larsen et al. "Molecular cloning, sequence, and expression of a human GDP-L-fucose: B-D-galactoside 2-a-L-fucosyltransferase cDNA that can form the H blood group antigen." Proc. Natl. Acad. Sci., USA, 87:6674-6678. (1990).

Lowe. "Molecular cloning, expression and uses of mammalian glycosyltransferases." Semin cell Biol., 2:289-307. (1991).

Lower et al. "Heterophil human antibodies recognize oncovirus envelope antigens: Epidemiological parameters and immunological specificity of the reaction." Virology, 109:409-417. (1981).

Maeurer et al. "Modulation of type II collagen-induced arthritis in DBA/1 mice by intravenous application of a peptide from the C1q-A chain." Immunobiol., 185:103-120. (1992).

Martinez et al. "Partial reconstitution of replication-competent retrovirus in helper cells with partial overlaps vetween vector and helper cell genomes." Human Gene Therapy, 7:705-712. (1996).

Matsubara et al. "Complement C4-derived monocyte-directed chemotaxis-inhibitory factor." Am. J. Path., 138:1279-1291. (1991).

Moffat et al. "Complement biosynthesis in human synovial tissue." Clin. Exp. Immunol., 78:54-60. (1989).

Mollnes et al. "Complement activation in rheumatoid arthritis evaluated by C3dg and the terminal complement complex." Arthr. Rheumat., 29:715-721. (1986).

Montz et al. "Regulation of the human autologous T cell proliferation by endogenously generated C5a." Cell. Immunol., 127:337-351. (1990).

Morgan et al. "Measurement of terminal complement complexes in rheumatoid arthritis." Clin. Exp. Immunol., 73:473-478. (1988).

Morgan et al. "Native type II collagen-induced arthritis in the rat." Arthr. Rheumat., 24:1356-1362. (1981).

Mori et al. "Expression of a transgenic T cell receptor β chain enhances collagen-induced arthritis." J. Exp. Med., 176:381-388. (1992).

Moxley and Ruddy. "Elevated C3 anaphylatoxin levels in synovial fluids from patients with rheumatoid arthritis." Arthr. Rheumat., 28:1089-1095. (1985).

Mulligan, R. "The basic science of gene therapy." Science, 260:926-931. (1993).

Myers et al. "A CD4 cell is capable of transferring suppression of collagen-induced arthritis." J. Immunol., 143:3976-3980. (1989).

McNeamey et al., "Herpes simplex virus glycoproteins gC-1 and gC-2 bind to the third component of complement and provide protection against complement-mediated neutralization of viral infectivity." J. Exp. Med. 166:1525-1535. (1987).

Nakajima et al. "Cell-mediated transfer of collagen-induced arthritis in mice and its application to the analysis of the inhibitory effects of interferon-gamma and cyclophosphamide." Clin. Exp. Immunol., 92:328-335. (1993).

Neething et al. "Protection of pig kidney (PK15) cells from the cytotoxic effect of anti-pig antibodies by a-galactosyl oligosaccharides." Transplantation, 57:959-963. (1994).

Oleesky et al. "Terminal complement complexes and C1/C1 inhibitor complexes in rheumatoid arthritis and other arthritic conditions." Clin. Exp. Immunol., 84:250-255. (1991).

Olmez et al. "C3 activation products, C3 containing immune complexes, the terminal complement complex and native C9 in patients with rheumatoid arthritis." Scand. J. Rheumatol., 20:183-189. (1991).

Olsen et al. "Clinical correlations with serum C1q levels in patients with rheumatoid arthritis." Arthr. Rheumat., 34:187-191. (1991).

Osman et al. "Characterization of the T cell receptor repertoire causing collagen arthritis in mice." J. Exp. Med., 177:387-395. (1993).

Peake et al. "Differences in the metabolism of C4 isotypes in patients with complement activation." Clin. Exp. Immunol., 78:49-53. (1989).

Peterman et al. "Role of $\gamma\delta$ T cells in murine collagen-induced arthritis." J. Immunol, 151:6546-6558. (1993).

Ram et al. "Toxicity studies of retroviral-mediated gene transfer for the treatment of brain tumors." J. Neurosurg., 79:400-407. (1993).

Reife et al. "SWR mice are resistant to collagen-induced arthritis but produce potentially arthritogenic antibodies." Arth. Rheumat., 34:776-781. (1991).

Repik et al. "Differential host-dependent expression of a-galatosyl epitopes on viral glycoproteins: a study of eastern equine encephalitis virus as a model." J. Gen. Virol., 75:1177-1181. (1994).

Rother et al. "Inhibitition of complement-mediated cytolysis by the terminal complement inhibitor of herpesvirus saimiri." J. Virol., 68:730-737. (1994).

Rother et al. "Protection of retroviral vector particles in human blood through complement inhibition." Human Gene Therapy, 6:429-435. (1995).

Rother et al. "A novel mechanism of retrovirus inactivation in human serum mediated by anti-a-galactosyl Natural antibody." J. Exp. Med. 182:1345-1355. (1995).

Sandrin et al. "Biochemical features of pig to human xenografts." J. leukocyte biolk, O (suppl):66. (1993).

Sandrin et al. "Anti-pig IgM antibodies in human serum react predominantly with gal (a1-3) gal epitopes." Proc Ntl Acad. Sci., USA 90:11392-11395. (1993).

Sandrin et al. "Gal a(1-3) gal, the major xenoantigen (s) reconized in pigs by human natural antibodies." Immunol. review, 141:160-190. (1994).

Saura et al. "Damage of cultured chondrocytes by hydrogen peroxide derived from polymorphonuclear leukocytes: A possible mechanism of cartilage degradation." Rheumat. Int., 12:141-146. (1992).

Seki et al. "Type III collagen-induced murine arthritis—I. Induction and perpetuation of arthritis require synergy between humoral and cell-mediated immunity." J. Immunol., 140:1477-1484. (1988).

Seki et al. "Type II collagen-induced murine arthritis: Induction of arthritis depends on antigen-presenting cell function as well as susceptibility of host to an anticollagen immune response." J. Immunol., 148:3093-3099. (1992).

Sherwin et al. "Complement-mediated lysis of type-C virus: EFfect of primate and human sera on various retroviruses." Int J. Cancer, 21:6-11. (1978).

Shingu et al. "Complement degradation products in rheumatoid arthritis synovial fluid." Br. J. Rheumat, 33:73-74. (1994).

Snyder et al. "Specificity of human antibodies to oncovirus glycoproteins: Recognition of antigen by natural antibodies directed against carbohydrate structures." Proc. Natl. Acad. Sci., USA 77:1622-1626. (1980).

Spear et al. "Direct binding of complement component C1q to human immunodeficiency virus (HIV) and human T lymphotrophic virus-1 (HTLV-1) coinfected cells." AIDS Research human retrovirus, 7:579-585. (1991).

Spinella and Stuart. "Author's Response." Immunogenet, 35:73-74. (1992).

Takuechi et al. "Type c retrovirus inactivation by human complement is determined by both the viral genome and the producer cell." J. Virol. 68:8001-8007. (1994).

Terato et al. "Induction of arthritis with monoclonal antibodies to collagen." J. Immunol., 148:2103-2108. (1992).

Thall et al. "Distribution of Galal-3galB1-4GlcNAc residues on secreted mammalian glycoproteins (Thyroglobulin, fibrinogen, and Immunoglobulin G) as measured by a sensitive solid-phase radioimmunoassy." Biochemistry, 29:3959-3965. (1990).

Thiry et al. "Factors which influence inactivation of vesicular stomatitis virus by fresh human serum." Virology, 87:384-393. (1978).

Thorbecke et al. "Involvement of endogenous tumor necrosis factor $\alpha$ and transforming growth factor $\beta$ during induction of collagen type II arthritis in mice." Proc. Natl. Acad. Sci., USA, 89:7375-7379. (1992).

van Lent et al. "Catioinic immune complex arthritis in mice—a new model." AM . J. Path., 140:1451-1461. (1992).

Vaughn et al. "Biochemical analysis of pig xenoantigens detected by human antibodies." Transplantation Proc. 25:2919-2920. (1993).

Ward and Zvaifler. "Complement-derived leukotactic factors in inflammatory in inflammatory synovial fluids of humans." J. Clin. Invest., 50:606-616. (1971).

Ward. "Complement-dependent phlogistic factors in rheumatoid synovial fluids." Anna NY Acad. Sci., 256:169-176. (1975).

Watson and Townes. "Genetic susceptibility to murine collagen II autoimmune arthritis." J. Exp. Med., 162:1878-1891. (1985).

Watson et al. "Passive transfer studies with type II colagen antibod in B10.D2/old and new line and C57B1/6 normal and beige (Chediak-Highashi) strains: Evidence of important roles for C5 and multiple inflammatory cell types in the development of erosive arthritis." Arthr. Rheumat., 30:460-465. (1987).

Welsh et al. "Human serum lyses RNA tumor viruses." Natural, 257:612-614. (1975).

Welsh et al. "Inactivation and lysis of oncornaviruses by human serum." Virology 74:432-440. (1976).

Widner et al. "Immunological aspects of grafting in the mammalian central nervous system. A review and speculative synthesis." Brain Res. Rey., 13:287-324. (1988).

Williams et al. "Successful transfer of collagen-induced arthritis to severe combined immunodeficient (SCID) mice." Clin. Exp. Immunol., 88:455-460. (1992).

Wurzner et al. "Inhibition of terminal complement complex formation and cell lysis by monoclonal antibodies." Complement Inflamm., 8:328-340. (1991).

Zvaifler. "Breakdown products of C'3 in human synovial fluids." J. Clin. Invest. 48:1532-1542. (1969).

Zvaifler. "Rheumatoid factor and the fixation of complement." Anna NY Acad. Sci., 168:146-160. (1969).

Zvaifler. "Rheumatoid synovitis—Extravascular immune complex disease." Arthr. Rheumat., 17-297-305. (1974).

Zvailer. "Studies on hemolytic complement in synovial fluids." Univ. Michigan Med. Ctr. J., 234-237. (1968).

* cited by examiner

METHODS FOR THE TREATMENT OF INFLAMMATORY JOINT DISEASE

RELATED APPLICATIONS

This application is a continuation of U.S. patent application Ser. No. 08/867,612, filed Jun. 2, 1997 now abandoned, which is a continuation of U.S. patent application Ser. No. 08/311,489, filed Sep. 23, 1994, abandoned, all of which are incorporated herein by reference.

FIELD OF THE INVENTION

The present invention relates to methods for the treatment of inflammatory joint disease. In particular, the invention relates to the use of blockers of complement component C5 ("C5 blockers") as pharmaceutical agents to treat established joint inflammation.

BACKGROUND OF THE INVENTION

I. The Complement System

The complement system acts in conjunction with other immunological systems of the body to defend against intrusion of cellular and viral pathogens. There are at least 25 complement proteins, which are found as a complex collection of plasma proteins and membrane cofactors. The plasma proteins (which are also found in most other body fluids, such as lymph, bone marrow, synovial fluid, and cerebrospinal fluid) make up about 10% of the globulins in vertebrate serum. Complement components achieve their immune defensive functions by interacting in a series of intricate but precise enzymatic cleavage and membrane binding events. The resulting complement cascade leads to the production of products with opsonic, immunoregulatory, and lytic functions.

The complement cascade progresses via the classical pathway or the alternative pathway. These pathways share many components, and, while they differ in their early steps, both converge and share the same terminal complement components responsible for the destruction of target cells and viruses.

The classical complement pathway is typically initiated by antibody recognition of and binding to an antigenic site on a target cell. This surface bound antibody subsequently reacts with the first component of complement, C1. The C1 thus bound undergoes a set of autocatalytic reactions that result in, inter alia, the induction of C1 proteolytic activity acting on complement components C2 and C4.

This activated C1 cleaves C2 and C4 into C2a, C2b, C4a, and C4b. The function of C2b is poorly understood. C2a and C4b combine to form the C4b,2a complex, which is an active protease known as classical C3 convertase. C4b,2a acts to cleave C3 into C3a and C3b. C3a and C4a are both relatively weak anaphylatoxins that may induce degranulation of mast cells, resulting in the release of histamine and other mediators of inflammation.

C3b has multiple functions. As opsonin, it binds to bacteria, viruses and other cells and particles and tags them for removal from the circulation. C3b can also form a complex with C4b,C2a to produce C4b,2a,3b, or classical C5 convertase, which cleaves C5 into C5a (another anaphylatoxin), and C5b. Alternative C5 convertase is C3b, Bb, C3b and performs the same function. C5b combines with C6 yielding C5b,6, and this complex combines with C7 to form the ternary complex C5b,6,7. The C5b,6,7 complex binds C8 at the surface of a cell membrane. Upon binding of C9, the complete membrane attack complex (MAC) is formed (C5b-9) which mediates the lysis of foreign cells, microorganisms, and viruses.

Further discussions of the classical complement pathway, as well as a detailed description of the alternative pathway of complement activation, can be found in numerous publications including, for example, Roitt, et al., 1988, and Muller-Eberhard, 1988.

II. Joint Inflammation

A variety of common medical disorders have as a common element the inflammation of the patient's joints. In the United States alone, millions of patients suffer from such joint inflammation. Afflicted individuals are frequently disabled, and the costs of medical care for patients suffering from such disorders are significant. While numerous means are available for treatment of joint inflammation, and new treatments continue to become available, none of these is as safe and effective as could be desired, and there has thus been a long felt need for new approaches and better methods to control joint inflammation.

Clinically, joint inflammation is associated with joint stiffness, pain, weakness, and sometimes joint fatigue. Uniformly, the joint is tender and swollen, and often erythematous. Diagnosis of the inflammatory nature of the joint disease is frequently based upon this typical clinical presentation as well as upon radiographic examination and aspiration and examination of synovial joint fluid. Examination of joint fluid of an inflamed joint generally reveals elevation of various markers of inflammation, such as, leukocytes (including neutrophils), antibodies, cytokines, cell adhesion molecules, and complement activation products (De Clerck et al., 1989; Heinz et al., 1989; Moffat et al., 1989; Peake et al., 1989; Brodeur et al., 1991; Firestein et al., 1991; Matsubara et al., 1991; Olsen et al., 1991; Oleesky et al., 1991; Jose et al., 1990; Zvaifler, 1968; Zvaifler, 1969a; Zvaifler, 1969b; Zvaifler, 1974; Ward and Zvaifler, 1971; Ward, 1975; Moxley and Ruddy, 1985; Mollnes et al., 1986; Auda et al., 1990; Olmez et al., 1991; Kahle et al., 1992; Koch et al., 1994; Thorbecke et al., 1992; Saura et al., 1992; Feldman et al., 1990; Feldman et al., 1991; Fong et al., 1994; Harigi et al., 1993; Morgan et al., 1988; Shingu et al., 1994; Abbink et al., 1992; and Corvetta et al., 1992). Radiographic examination of affected joints generally reveals soft tissue swelling and/or erosive changes.

Joint inflammation is associated with a group of diseases that are referred to medically as arthridities (types of arthritis). The term "arthritis" is used medically to generally describe diseases of the joints. The term, however, is also used to describe certain medical conditions, of which rheumatoid arthritis (RA) is the primary example, that consist of a multiplicity of different pathologic manifestations, including, but by no means limited to, joint disease.

Discussions of arthritis may thus include diseases such as RA, where joint disorders are only one facet of the varied pathologies associated with the disease. The present invention is directed specifically to the joint disorder aspects of these diseases. The methods of the invention, however, may also have beneficial effects on non-joint-associated pathologies. For example, use of the methods of the invention to treat established joint inflammation associated with RA, psoriasis, lupus, and other disorders may also provide therapeutic benefits impacting on some of the other pathologic manifestations of these multifaceted disease states, such as vascular inflammation and nephritis (see, for example, Wurzner, et al., Complement Inflamm. 8:328-340, 1991; U.S. application Ser. No. 08/217,391 filed on Mar. 23, 1994, abandoned; U.S. application Ser. No. 08/236,208 filed on May 2, 1994, now U.S. Pat. No. 6,074,642; and Sims, et al., U.S. Pat. No. 5,135,916).

It should be noted that the present invention is not concerned with all types of joint disorders, but only those involving inflammation. Thus, for example, the invention is applicable to the treatment of late-stage osteoarthritis (OA), which is an inflammatory joint disease, but generally not to early stage OA, which does not typically have a significant inflammatory component.

Detailed discussions of the arthridities can be found in numerous medical texts, including Arnett, 1992. *Cecil Textbook of Medicine*, Wyngaarden et al. (eds.), W. B. Saunders Company, Philadelphia, Chapter 258, pp. 1508-1515; Lipsky, 1994. *Harrison's Principles of Internal Medicine, 13th Ed.*, Isselbacher et al. (eds), McGraw-Hill, Inc., New York, Chapter 285, pp. 1648-1655; and McCarty and Koopman, 1993. *Arthritis and Allied Conditions, 12th Ed.* Lea and Febiger, Philadelphia. As discussed in detail in these and other texts, and reviewed below, joint inflammation is associated with numerous local and systemic disease processes.

Factors Associated with Joint Inflammation

Joint inflammation is a complex process involving, among other things, activation of both cellular and humoral immune responses.

Cellular immune responses include infiltration by white blood cells, predominantly neutrophils (also referred to as polymorphonuclear cells or PMNs). Mononuclear white blood cell infiltrates are also common in many inflamed joints. Infiltrating mononuclear cells, including T lymphocytes (as well as cells resident within the joint such as synovial cells, fibroblasts, and endothelial cells) are activated and contribute to the production of multiple inflammatory cytokines including TNF-α, IL-1, IFN-γ, IL-2, IL-6, IL-8, GM-CSF, PDGF and FGF, these latter two being capable of stimulating synovial cell proliferation.

All of these cytokines are thought to play a role in inducing the production of numerous other inflammatory factors as well as various other mediators of tissue degradation. These factors and mediators of degradation include products of arachidonic acid metabolism (that are active in various intracellular signal transduction pathways), reactive oxygen intermediates, and degradative enzymes such as collagenase, stromelysin, and other neutral proteases, all of which can further contribute to the inflammatory response and to tissue destruction.

Cellular infiltration into the synovium is enhanced by the upregulation of cell adhesion molecules such as selecting, LFA-3, and members of the ICAM family of Ig-like cell adhesion molecules on cells within the joint. These adhesion molecules promote the infiltration of activated white blood cells into the affected joint by stimulating leukocyte (including lymphocyte) adhesion, migration, and activation.

The humoral immune system also contributes to joint inflammation. Antibodies are produced within inflamed joints in such diseases as RA, JRA and OA (see below) and generate localized immune complexes that can activate the complement system. As discussed above in greater detail, activated complement components can have cytolytic, cell activating, anaphylatoxic, and chemotactic effects.

These multifactorial inflammatory responses lead to cartilage destruction and bone erosion that ultimately result in the joint deformity seen in patients with chronic joint inflammation.

In view of the complex nature of joint inflammation, a variety of theories, many of which are conflicting, have been proposed in the art to explain the relative importance of the various factors involved. Notwithstanding extensive work, there remains a basic controversy in the art as to the relative roles of the cellular and humoral immune systems in joint inflammation, including what role complement plays in such inflammation. See, for example, Andersson and Holmdahl, 1990; Brahn and Trentham, 1989; Chiocchia et al., 1990; Chiocchia et al., 1991; Durie et al., 1993; Goldschmidt et al., 1990; Goldschmidt and Holmdahl, 1991; Holmdahl et al., 1985; Holmdahl et al., 1989; Holmdahl et al., 1990; Hom et al., 1988; Hom et al., 1992; Hom et al., 1993; Mori et al., 1992; Myers et al., 1989A; Nakajima et al., 1993; Osman et al., 1993; Peterman et al., 1993; Seki et al., 1988; Seki et al., 1992; Terato et al., 1992; Watson et al., 1987; and, in particular, the following reports relating to the complement system and/or the relative roles of T cells and complement components in joint inflammation: Andersson et al., 1991; Andersson et al., 1992; Banerjee et al., 1988B; Banerjee et al., 1989; David, 1992; Fava et al., 1993; Haqqi et al., 1989; Kakimoto et al., 1988; Maeurer et al., 1992; Morgan et al., 1981; Moxley and Ruddy, 1985; Reife et al., 1991; Spinella et al., 1991; Spinella and Stuart, 1992; van Lent et al., 1992; Watson et al., 1987; Watson and Townes, 1985; and Williams et al., 1992A. To date, these wide ranging studies have not led to effective treatments for established joint inflammation based on modulation of the complement system and, in particular, based on the use of C5 blockers.

The studies of the prophylactic effects of C5 blockers reported below in Example 2 were designed to determine if C5 was an appropriate and effective target for pharmacological modulation of the humoral immune system in order to prevent joint inflammation. The surprising effectiveness of C5 blockers in preventing onset of joint inflammation led to the design and execution of the studies reported in Example 1 in which C5 blockers were used to treat established inflammation. At the outset of these experiments, it was anticipated that such treatment would have little measurable effect upon established joint inflammation, as it was supposed that C5 was more important early in the disease process when the chemotactic activity of C5a would trigger the infiltration of inflammatory cells. It was further supposed that the involvement of T cells in established disease would continue to provide significant inflammatory stimuli even in the absence of C5 activity. As shown by the results of Example 1 this expectation was incorrect in that C5 blockers were found to be surprisingly effective in arresting and/or reducing the inflammation of joints which were already inflamed, while at the same time inhibiting the spread of inflammation to unaffected joints.

Diseases Commonly Associated with Joint Inflammation

Rheumatoid arthritis (RA) and juvenile onset rheumatoid arthritis (JRA) are chronic multisystem diseases of unknown cause. RA affects approximately 1% of the population, with women affected three times more commonly than men. The onset is most frequent during the fourth and fifth decades of life. RA and JRA are systemic diseases with numerous pathologic manifestations in addition to their joint inflammatory aspects. In RA, these manifestations include RA vasculitis (inflammation of the blood vessels), which can affect nearly any organ system and can cause numerous pathologic sequelae including polyneuropathy, cutaneous ulceration, and visceral infarction. Pleuropulmonary manifestations include pleuritis, interstitial fibrosis, pleuropulmonary nodules, pneumonitis, and arteritis. Other manifestations include the development of inflammatory rheumatoid nodules on a variety of periarticular structures such as extensor surfaces, as well as on pleura and meninges. Weakness and atrophy of skeletal muscle are common.

The joint inflammation aspects of RA present as persistent inflammatory synovitis, usually involving peripheral joints in a symmetric distribution. In general, the complex intraarticular inflammatory response seen in RA is of the type described above in the general discussion of joint inflammation.

Many patients with systemic lupus erythematosis (SLE) also develop joint inflammation referred to as lupus arthritis. SLE is an autoimmune disease of unknown cause in which numerous different cells, tissues, and organs are damaged by pathogenic autoantibodies and immune complexes. Clinical manifestations of SLE are numerous and include a variety of maculopapular rashes, nephritis, cerebritis, vasculitis, hematologic abnormalities including cytopenias and coagulopathies, pericarditis, myocarditis, pleurisy, gastrointestinal symptoms, and the aforementioned joint inflammation.

Osteoarthritis (OA) represents the most common joint disease of mankind, and OA of the knee is the leading cause of chronic disability in developed countries. It is manifested by pain, stiffness, and swelling of the involved joints. Articular cartilage, responsible for the most critical mechanical functions of the joint, is the major target tissue of OA. The breakdown of articular cartilage in OA is mediated by various enzymes such as metalloproteinases, plasmin, and cathepsin, which are in turn stimulated by various factors that can also act as inflammatory mediators. These factors include cytokines such as interleukin-1, which is known to activate the pathogenic cartilage and synovial proteases.

The identification of above normal levels of immunoglobulin in cartilage in generalized OA and the demonstration of type II collagen-specific antibodies in some OA patients provide evidence of a role for immune activation in this disease state (see, for example, Jasin, 1989). The observation that OA rarely remains monoarticular also suggests that this disease is a systemic disorder of articular cartilage. Synovial inflammation becomes more frequent as the disease progresses. In fact, in late stage OA, histologic evidence of synovial inflammation may be as marked as that in the synovium of patients with RA-associated joint inflammation.

Psoriatic arthritis is a chronic inflammatory joint disorder that affects 5 to 8% of people with psoriasis. A significant percentage of these individuals (one-fourth) develop progressive destructive disease. Twenty-five percent of psoriasis patients with joint inflammation develop symmetric joint inflammation resembling the joint inflammation manifestations of RA, and over half of these go on to develop varying degrees of joint destruction.

Other Diseases Associated with Joint Inflammation

A variety of other systemic illnesses have joint inflammation as a prominent feature of the clinical presentation.

Peripheral joint inflammation occurs in as many as one-fifth of patients with inflammatory bowel disease. The joint inflammation is acute, associated with flare-ups of the bowel disease, and is manifested by swollen, erythematous, warm, and painful joints. Synovial fluids of sufferers have an acute inflammatory exudate of mostly neutrophils, and radiographs demonstrate soft tissue swelling and effusions.

The synovitis that accompanies hepatitis B resembles serum sickness, with abrupt onset of fever and articular inflammation. There is generally a symmetric inflammation of joints including the knee, shoulder, wrist, ankles, elbow, and the joints of the hands. Immune complexes containing hepatitis B antigens are present in serum and synovium, lending support to the concept that the synovitis is immunologically mediated. Other viral diseases associated with joint inflammation include rubella, human immunodeficiency virus infection, coxsackieviral, and adenoviral infections.

An immune complex mediated joint inflammation is also associated with intestinal bypass surgery, and joint inflammation is a prominent manifestation of Whipple's disease, or intestinal lipodystrophy, where fever, edema, serositis, lymphadenopathy, uveitis, and cerebral inflammation are associated findings. Furthermore, potentially immunologically-related joint inflammation is an associated sequelum of infectious endocarditis and certain spirochetal infections, most notably infection with *Borrelia burgdorferi*, the causative organism of Lyme disease.

Primary Sjögrens syndrome is a chronic, slowly progressive autoimmune disease characterized by lymphocytic infiltration of the exocrine glands resulting in xerostomia and dry eyes. One-third of patients present with systemic manifestations, including vasculitis, nephritis, mononeuritis multiplex, and, most commonly, joint inflammation.

Ankylosing spondylitis (AS) is an inflammatory disorder of unknown cause that affects primarily the axial skeleton, but peripheral joints are also affected. Its incidence correlates with the HLA-B27 histocompatibility haplotype, and immune-mediated mechanisms are further implicated by elevated serum levels of IgA and an inflammatory joint histology with similar characteristics to those seen in the joint inflammation aspects of RA. Thus, synovial fluid from inflammatory peripheral joints in AS is not distinctly different from that of other inflammatory joint diseases.

Reactive arthritis (ReA) refers to acute nonpurulent joint inflammation complicating an infection elsewhere in the body. Reactive arthritis is believed to be immunologically mediated. Included in this category is the constellation of clinical findings often referred to as Reiter's syndrome or Reiter's disease. In addition to joint inflammation, this syndrome affects the skin, eyes, mucous membranes, and less commonly the heart, lungs, and nervous system. Reiter's syndrome may follow enteric infections with any of several *Shigella, Salmonella, Yersinia*, and *Campylobacter* species, and genital infections with *Chlamydia trachomatous*. The histology of joints affected by this syndrome is similar to that seen in other types of joint inflammation. The joint inflammation is usually quite painful, and tense joint effusions are not uncommon, especially in the knee. The joint inflammation is usually asymmetric and additive, with involvement of new joints occurring over a period of a few days to several weeks.

III. Current Therapies

Current therapies for the various types of joint inflammation discussed above include the administration of anti-inflammatory drugs such as non-steroidal drugs, including aspirin, and non-specific immunosuppressive drugs, such as gold compounds, corticosteroids, penicillamine, hydroxychloroquine, methotrexate, azathioprine, alkylating agents such as cyclophosphamide, and sulfasalazine. Administration of each of these agents is sometimes associated with severe side effects and toxicities. Patients receiving certain of these treatments are also exposed to the dangers of opportunistic infection and increased risk of neoplasia associated with generalized immunosuppression. In addition to the medical texts cited above, discussions of drugs used to treat established joint inflammation can be found in *Goodman and Gilman's The Pharmacological Basis of Thera-* peutics 18th Ed., Gilman et al. (eds.) 1990, Pergamon Press, Inc., New York, Chapter 26, pp. 638-681; *Physician's Desk Reference* 47*th Ed.*, 1993, Medical Economics Co., Inc., Montvale, N.J.; *The United States Pharmacopeia* 22*nd Ed.*, 1989, Mack Printing Co., Easton, Pa.; *Drug Evaluations Annual* 1991, 1990, American Medical Association, Milwaukee, Wis.; and Cash and Klippel, 1994, *N. Eng. J. Med.* 330, pp. 1368-1375.

In addition to pharmacologic treatments, relief of the symptoms of joint inflammation is sometimes achieved with warm or cold soaks. Surgical intervention using tendon release procedures and/or joint replacement procedures is frequently the last resort for treatment of chronic joint inflammation. Such orthopedic surgery is associated with increased infection and prostheses have limited life spans.

New therapeutic approaches currently being developed include attempts to address various elements of the cellular immune response contributing to the inflammatory cascade present in inflamed joints. These approaches include the administration of therapeutic preparations including anti-T cell and/or anti-cytokine agents (see, for example, Banerjee et al., 1988A; Cannon et al., 1990; Chiocchia et al., 1991; Elliot et al., 1993; Fava et al., 1993; Fujimori et al., 1993; Griswold et al., 1988; Hom et al., 1988; Hom et al., 1991; Hom et al., 1993; Inoue et al., 1993; Kakimoto et al., 1992; Kleinau et al., 1989; Myers et al., 1989b; Myers et al., 1993; Nagler-Anderson et al., 1986; Nishikaku and Koga, 1993; Peterman et al., 1993; Piguet et al., 1992; Smith et al., 1990; Spannaus-Martin et al., 1990; Thompson et al., 1988; Trentham et al., 1993; Williams et al., 1992b; Williams et al., 1994; and Wolos et al., 1993).

SUMMARY OF THE INVENTION

In view of the foregoing, it is an object of the present invention to provide a new approach for treating established joint inflammation.

To achieve this goal, the invention provides methods involving the use of blockers of complement component C5 as pharmaceutical agents to accomplish therapeutic treatment of established joint inflammation. The C5 blockers are administered to animals, e.g., humans, having at least one inflamed joint. The blockers can be administered systemically or locally. They achieve a reduction or stabilization of the inflammation of joints that are already inflamed and inhibit the spread of inflammation to unaffected joints.

As used herein, a "C5 blocker" is a compound that directly interacts with C5, C5a, and/or C5b, i.e., a compound that directly binds to or directly modifies (i.e., by a direct chemical reaction) one of these complement components, so as to inhibit the formation of and/or physiologic function of C5a and/or C5b. Preferably, the formation and/or physiologic functions of both C5a and C5b are inhibited by the C5 blocker.

Direct interaction with C5, C5a, and/or C5b has the important advantage that other components of the complement cascade may be left intact. In particular, the opsonization functions associated with the activation of complement component C3 by a C3 convertase to yield C3a and C3b may be left intact allowing for continued clearance of foreign particles and substances from the body by the action of C3b. The most preferred C5 blockers are those which are of this type, i.e., those that do not interfere with C3b function.

As demonstrated by the examples presented below, in accordance with the invention, it has been surprisingly found that treatment with C5 blockers will arrest and, in many cases, at least partially reverse the disease process at an inflamed joint, while at the same time preventing progression of joint inflammation to non-affected joints. Given the prior understanding in the art regarding the role of the cellular immune system in joint inflammation (see above), one would not have expected that a C5 blocker would have such a dramatic beneficial effect on established joint inflammation.

The accompanying figures, which are incorporated in and constitute part of the specification, illustrate certain aspects of the invention, and together with the description, serve to explain the principles of the invention. It is to be understood, of course, that both the figures and the description are explanatory only and are not restrictive of the invention.

BRIEF DESCRIPTION OF THE DRAWINGS

FIG. 1*a* shows a paw joint from a normal mouse; FIG. 1*b* shows an initially affected paw joint from a control treated mouse, where the joint exhibits extensive bone erosion with severe inflammatory cell infiltration and thickening of the synovial membrane; and FIG. 1*c* shows an initially affected paw joint from a C5 blocker treated mouse showing preserved joint structure with some degree of synovial membrane thickening and a surprising lack of polymorphonuclear cell infiltration compared with the initially affected joint from the control group (FIG. 1*b*).

FIG. 2*a* shows a comparison of mean joint inflammation (JI) index values. Data represent mean JI index +/− standard error. Solid circles are C5 blocker treated mice (n=6). Open circles are control treated mice (n=4). FIG. 2*b* shows a comparison of paw thickness of initially affected joints. After onset of joint inflammation, control paw thickness increased significantly compared to treated or normal (N) paws. Data represent mean thickness +/− SE. Solid circles are C5 blocker treated mice (n=8). Open circles are control treated mice (n=4).

FIGS. 3*a-d* show measurements from initially affected paws of paired animals; FIG. 3*e* shows measurements from initially affected paws of two unpaired treated animals and the mean control measurements of FIG. 2*b*.

FIG. 4*a* shows a paw joint from a normal mouse; FIG. 4*b* shows an affected paw joint from a control treated mouse, where inflammatory cell infiltration, thickening of the synovial membrane and bone erosion by the expanding synovial pannus are visible; and FIG. 4*c* shows a typical paw joint from a C5 blocker treated mouse showing only subclinical thickening of the synovial membrane.

FIG. 5 shows that treatment with a C5 blocker prevents joint inflammation.

FIG. 6 shows the effects of C5 blocker treatment on collagen-specific humoral and cellular responses.

DESCRIPTION OF THE PREFERRED EMBODIMENTS

Figure 1A:
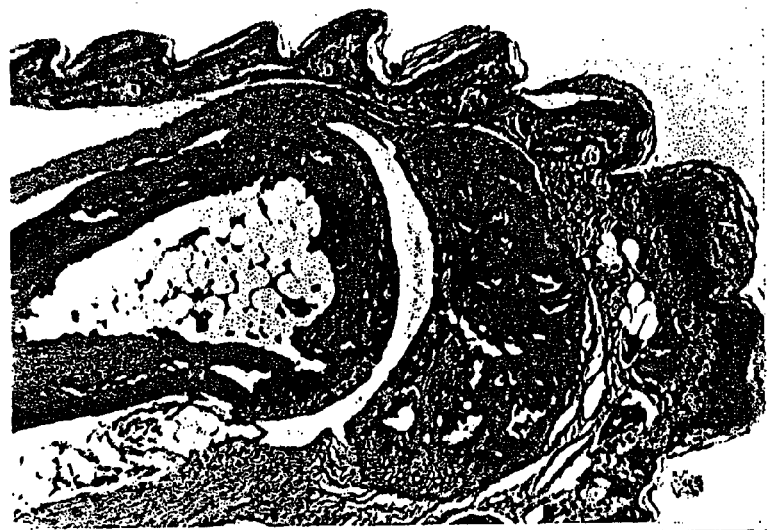
FIGS. 1*a-c* are photomicrographs of joints stained with Hematoxylin and Eosin illustrating the use of a C5 blocker to stop the progression of established joint inflammation.

As discussed above, the present invention relates to a method for treating established joint inflammation by the administration of a C5 blocker or a combination of C5 blockers to a patient in need of such treatment. As used herein, "established joint inflammation" means that the patient has at least one inflamed joint at the time treatment is commenced.

Such C5 blockers comprise proteins (including antibodies), peptides, and other molecules that directly interact with C5, C5a, and/or C5b, so as to inhibit the formation of and/or physiologic function of C5a and/or C5b. Examples of non-protein molecules of this type include K-76 COOH, (see Hong et al., 1979), and substituted dihydrobenzofurans, spirobenzofuran-2(3H)-cycloalkanes, and their open chain intermediates, (see Sindelar et al., U.S. Pat. No. 5,173,499), that are reported to directly interact with C5, C5a, and/or C5b. Preferably, the C5 blocker or blockers inhibit the formation of and/or physiologic function of both C5a and C5b.

The concentration and/or physiologic activity of C5a and C5b in a body fluid can be measured by methods well known in the art. For C5a such methods include chemotaxis assays, RIAs, or ELISAs (see, for example, Ward and Zvaifler, 1971; Jose et al., 1990; Wurzner et al., 1991). For C5b, hemolytic assays or assays for soluble C5b-9 as discussed herein can be used. Other assays known in the art can also be used. Using assays of these or other suitable types, candidate C5 blockers, now known or subsequently identified, can be screened in order to 1) identify compounds that are useful in the practice of the invention and 2) determine the appropriate dosage levels of such compounds. Examples 2, 4, and 6-8 illustrate the use of hemolytic and soluble C5b-9 assays with C5 blockers comprising monoclonal antibodies.

Blockers affecting C5a are preferably used at concentrations providing substantial reduction (i.e., reduction by at least about 25%) in the C5a levels present in at least one blood-derived fluid of the patient, e.g., blood, plasma, or serum, following activation of complement within the fluid. Alternatively, they are used at concentrations providing at least about a 10% reduction in the C5a levels present in the synovial fluid of an inflamed joint.

Similarly, blockers affecting C5b are preferably used at concentrations providing substantial reduction (i.e., reduction by at least about 25%) in the C5b levels present in at least one blood-derived fluid of the patient following activation of complement within the fluid. Alternatively, they are used at concentrations providing at least about a 10% reduction in the C5b levels present in the synovial fluid of an inflamed joint. In the case of C5b, such concentrations can be conveniently determined by measuring the cell-lysing ability (e.g., hemolytic activity) of complement present in the fluid or the levels of soluble C5b-9 present in the fluid (see, for example, Example 6 below). Accordingly, a preferred concentration for a C5 blocker that affects C5b is one that results in a substantial reduction (i.e., a reduction by at least about 25%) in the cell-lysing ability of the complement present in at least one of the patient's blood-derived fluids. Reductions of the cell-lysing ability of complement present in the patient's body fluids can be measured by methods well known in the art such as, for example, by a conventional hemolytic assay such as the hemolysis assay described by Kabat and Mayer, 1961, pages 135-139, or a conventional variation of that assay such as the chicken erythrocyte hemolysis method described below.

Preferred C5 blockers are relatively specific, and do not block the functions of early complement components. In particular, such preferred agents will not substantially impair the opsonization functions associated with complement component C3b, which functions provide a means for clearance of foreign particles and substances from the body.

C3b is generated by the cleavage of C3, which is carried out by classical and/or alternative C3 convertases, and results in the generation of both C3a and C3b. Therefore, in order not to impair the opsonization functions associated with C3b, preferred C5 blockers do not substantially interfere with the cleavage of complement component C3 in a body fluid of the patient (e.g., serum) into C3a and C3b.

Such interference with the cleavage of C3 can be detected by measuring body fluid levels of C3a and/or C3b, which are produced in equimolar ratios by the actions of the C3 convertases. Such measurements are informative because C3a and C3b levels will be reduced (compared to a matched sample without the C5 blocker) if cleavage is interfered with by a C5 blocker.

In practice, the quantitative measurement of such cleavage is generally more accurate when carried out by the measurement of body fluid C3a levels rather than of body fluid C3b levels, since C3a remains in the fluid phase whereas C3b is rapidly cleared. C3a levels in a body fluid can be measured by methods well known in the art such as, for example, by using a commercially available C3a EIA kit, e.g., that sold by Quidel Corporation, San Diego, Calif., according to the manufacturers specifications. Particularly preferred C5 blockers produce essentially no reduction in body fluid C3a levels following complement activation when tested in such assays.

Preferred C5 blocking agents include antibodies. The antibodies are preferably monoclonal, although polyclonal antibodies, which can be produced and screened by conventional techniques, can also be used if desired. Hybridomas producing monoclonal antibodies (mAbs) reactive with complement component C5 can be obtained using complement component C5, C5a, and/or C5b, preferably in purified form, as the immunogen.

The most preferred antibodies will prevent the cleavage of C5 to form C5a and C5b, thus preventing the generation of the anaphylatoxic activity associated with C5a and preventing the assembly of the membrane attack complex associated with C5b. As discussed above, in a particularly preferred embodiment, these C5 blocking antibodies will not impair the opsonization function associated with the action of C3b.

General methods for the immunization of animals (in this case with C5, C5a, and/or C5b), isolation of antibody producing cells, fusion of such cells with immortal cells (e.g., myeloma cells) to generate hybridomas secreting monoclonal antibodies, screening of hybridoma supernatants for reactivity of secreted monoclonal antibodies with a desired antigen (in this case the immunogen or a molecule containing the immunogen), the preparation of quantities of such antibodies in hybridoma supernatants or ascites fluids, and for the purification and storage of such monoclonal antibodies, can be found in numerous publications. These include: Coligan, et al., eds. *Current Protocols In Immunology*, John Wiley & Sons, New York, 1992; Harlow and Lane, *Antibodies, A Laboratory Manual*, Cold Spring Harbor Laboratory, New York, 1988; Liddell and Cryer, *A Practical Guide To Monoclonal Antibodies*, John Wiley & Sons, Chichester, West Sussex, England, 1991; Montz, et al., *Cellular Immunol*. 127:337-351, 1990; Wurzner, et al., *Complement Inflamm*. 8:328-340, 1991; and Mollnes, et al., *Scand. J. Immunol*. 28:307-312, 1988.

A description of the preparation of a mouse anti-human-C5 monoclonal antibody with preferred binding characteristics is presented below in Example 8. Wurzner, et al., 1991, describe the preparation of other suitable mouse anti-human-C5 monoclonal antibodies referred to as N19-8 and N20-9.

As used herein, the terms "antibody" or "antibodies" refer to immunoglobulins produced in vivo, as well as those produced in vitro by a hybridoma, and antigen binding fragments (e.g., Fab' preparations) of such immunoglobulins, as well as to recombinantly expressed (engineered) antigen binding proteins, including immunoglobulins, chimeric immunoglobulins, "humanized" immunoglobulins, antigen binding fragments of such immunoglobulins, single chain antibodies, and other recombinant proteins containing antigen binding domains derived from immunoglobulins. As used herein, the term "monoclonal" refers to any antibody that is not of polyclonal origin.

Publications describing methods for the preparation of engineered antibodies, in addition to those listed immediately above, include: Reichmann, et al., *Nature*, 332:323-327, 1988; Winter and Milstein, *Nature*, 349:293-299, 1991; Clackson, et al., *Nature*, 352:624-628, 1991; Morrison, *Annu Rev Immunol*, 10:239-265, 1992; Haber, *Immunol Rev*, 130:189-212, 1992; and Rodrigues, et al., *J Immunol*, 151: 6954-6961, 1993. Human or humanized antibodies are preferred for administration to human patients.

To achieve the desired reductions of body fluid parameters, such anti-C5 antibodies can be administered in a variety of unit dosage forms. The dose will vary according to the particular antibody. For example, different antibodies may have different masses and/or affinities, and thus require different dosage levels. Antibodies prepared as Fab' fragments or single chain antibodies will also require differing dosages than the equivalent native immunoglobulins, as they are of considerably smaller mass than native immunoglobulins, and thus require lower dosages to reach the same molar levels in the patient's blood.

Dosage levels of the antibodies for human subjects are generally between about 0.5 mg per kg and about 100 mg per kg per patient per treatment, and preferably between about 1 mg per kg and about 50 mg per kg per patient per treatment. In terms of body fluid concentrations, the antibody concentrations are preferably in the range from about 5 µg/ml to about 500 µg/ml.

Other C5 blockers can also be administered in a variety of unit dosage forms and their dosages will also vary with the size, potency, and in vivo half-life of the particular C5 blocker being administered.

Doses of C5 blockers will also vary depending on the manner of administration, the particular symptoms of the patient being treated, the overall health, condition, size, and age of the patient, and the judgment of the prescribing physician.

Subject to the judgement of the physician, a typical therapeutic treatment includes a series of doses, which will usually be administered concurrently with the monitoring of clinical endpoints such as number of joints involved, redness of joints, swelling of joints, mobility of joints, pain levels, etc., with the dosage levels adjusted as needed to achieve the desired clinical outcome.

The frequency of administration may also be adjusted according to various parameters. These include the clinical response, the plasma half-life of the C5 blocker, and the levels of the blocker in a body fluid, such as, blood, plasma, serum, or synovial fluid. To guide adjustment of the frequency of administration, levels of the C5 blocker in the body fluid may be monitored during the course of treatment.

Alternatively, for C5 blockers that affect C5b, levels of the cell-lysing ability of complement present in one or more of the patient's body fluids are monitored to determine if additional doses or higher or lower dosage levels are needed. Such doses are administered as required to maintain at least about a 25% reduction, and preferably about an 50% or greater reduction of the cell-lysing ability of complement present in blood, plasma, or serum, or at least about a 10% reduction of the cell-lysing ability of complement present in synovial fluid from an inflamed joint. The cell-lysing ability can be measured as percent hemolysis in hemolytic assays of the types described herein. A 10% or 25% or 50% reduction in the cell-lysing ability of complement present in a body fluid after treatment with the C5 blocker or blockers used in the practice of the invention means that the percent hemolysis after treatment is 90, 75, or 50 percent, respectively, of the percent hemolysis before treatment.

In yet another alternative, dosage parameters are adjusted as needed to achieve a substantial reduction of C5a levels in blood, plasma, or serum, or at least a 10% reduction of the C5a levels in the synovial fluid of an inflamed joint. As discussed above, C5a levels can be measured using the techniques described in Wurzner, et al., *Complement Inflamm* 8:328-340, 1991. Other protocols of administration can, of course, be used if desired as determined by the physician.

In a preferred embodiment, administration of the C5 blocker is initiated when the patient experiences a "flare up" of joint inflammation in which one or more affected joints becomes more swollen and takes on an erythematous (reddened) appearance.

Administration of the C5 blockers will generally be performed by a parenteral route, typically via injection such as intra-articular or intravascular injection (e.g., intravenous infusion) or intramuscular injection. Other routes of administration, e.g., oral (p.o.), may be used if desired and practicable for the particular C5 blocker to be administered.

For the treatment of established joint inflammation by systemic administration of a C5 blocker (as opposed to local administration, e.g., intra-articular injection into the inflamed joint) administration of a large initial dose is preferred, i.e., a single initial dose sufficient to yield a substantial reduction, and more preferably an at least about 50% reduction, in the hemolytic activity of the patient's serum. Such a large initial dose is preferably followed by regularly repeated administration of tapered doses as needed to maintain substantial reductions of serum hemolytic titer. In another embodiment, the initial dose is given by both local and systemic routes, followed by repeated systemic administration of tapered doses as described above.

Formulations suitable for injection, p.o., and other routes of administration are well known in the art and may be found, for example, in *Remington's Pharmaceutical Sciences*, Mack Publishing Company, Philadelphia, Pa., 17th ed. (1985). Parenteral formulations must be sterile and non-pyrogenic, and generally will include a pharmaceutically effective carrier, such as saline, buffered (e.g., phosphate buffered) saline, Hank's solution, Ringer's solution, dextrose/saline, glucose solutions, and the like. These formulations may contain pharmaceutically acceptable auxiliary substances as required, such as, tonicity adjusting agents, wetting agents, bactericidal agents, preservatives, stabilizers, and the like.

The formulations of the invention can be distributed as articles of manufacture comprising packaging material and a pharmaceutical agent which comprises the C5 blocker or blockers and a pharmaceutically acceptable carrier as appropriate to the mode of administration. The packaging material will include a label which indicates that the formulation is for use in the treatment of joint inflammation and may specifically refer to arthritis, rheumatoid arthritis, osteoarthritis, lupus arthritis, psoriatic arthritis, juvenile onset rheumatoid arthritis, reactive arthritis, Reiter's syndrome (Reiter's disease), or other diseases involving joint inflammation.

Without intending to limit it in any manner, the present invention will be more fully described by the following examples. The methods and materials which are common to various of the examples are as follows.

MATERIALS AND METHODS

Cell Lysis Assays

The cell-lysing ability of complement in various body fluid samples was determined using hemolytic assays performed as follows: Chicken erythrocytes were washed well in GVBS (Sigma Chemical Co. St. Louis, Mo., catalog No. G-6514) and resuspended to $2 \times 10^8$/ml in GVBS. Anti-chicken erythrocyte antibody (IgG fraction of anti-chicken-RBC antiserum, Intercell Technologies, Hopewell, N.J.) was added to the cells at a final concentration of 25 µg/ml and the cells were incubated for 15 min. at 23° C. The cells were washed 2× with GVBS and $5 \times 10^6$ cells were resuspended to 30 µL in GVBS. A 100 µL volume of body fluid test solution was then added to yield a final reaction mixture volume of 130 µL. As used herein, reference to the serum percentage and/or serum input in these assays indicates the percent of a body fluid (including serum, as well as other body fluids such as blood, plasma, or synovial fluid) in the 100 µL volume of body fluid test solution.

After incubation for 30 min. at 37° C., percent hemolysis was calculated relative to a fully lysed control sample. Hemolysis was determined by spinning the cells down and measuring released hemoglobin in the supernatant as the optical density at 415 nm.

A 50% reduction in hemolysis after treatment with the C5 blocker or blockers used in the practice of the invention means that the percent hemolysis after treatment was one half of the percent hemolysis before treatment.

Various hemolytic assays described below in the examples were performed using this chicken erythrocyte assay with the following body fluid inputs. For assays of mouse complement activity, the 100 µL volume of body fluid test solution contained 50 µL of diluted (in GVBS) mouse serum and 50 µL of human C5 deficient serum (Quidel Corporation, San Diego, Calif.). For assays of human complement activity, the body fluid test solution contained various concentrations of human plasma or serum, with hybridoma supernatants and/or GVBS being added to yield the final 100 µL volume. For the assays used to screen hybridoma supernatants discussed below in example 8 each 100 µL volume of serum test solution contained 50 µL of hybridoma supernatant and 50 µL of a 10% solution of human serum in GVBS, yielding a 5% human serum input.

Collagen Induced Joint Inflammation

Examples 1, 2, and 3 use a collagen induced joint inflammation system that has been employed since the 1970s as an animal model of human joint inflammation, particularly RA (see, for example, Trentham et al., 1977; Holmdahl et al., 1986; Boissier et al., 1987; Yoo et al., 1988). This model system was implemented using 8-12 week old male DBA/1LacJ mice that were purchased from The Jackson Laboratory (Bar Harbor, Me.).

Immunization

Bovine collagen II (B-CII) obtained from Elastin Products Company, Inc., Owensville, Mo., was dissolved in 0.01M acetic acid by stirring overnight at 4° C. at a concentration of 4 mg/ml. Complete Freund's adjuvant (CFA) was prepared by the addition of desiccated *Mycobacterium tuberculosis* H37RA (Difco, Detroit, Mich.) to incomplete Freunds adjuvant (Difco) at a concentration of 2 mg/ml. The solution of B-CII was emulsified in an equal volume of CFA and a 100 µl aliquot of this emulsion, containing 200 µg B-CII and 100 µg of *Mycobacterium*, was injected intradermally at the base of the mouse's tail. After 21 days, all mice were reimmunized using the identical protocol. This secondary CII reimmunization served primarily to boost the serum levels of anti-CII antibodies in the immunized mice. After CII reimmunization, the onset of joint inflammation (JI) and disease progression rise dramatically, characterized by the severe swelling and redness of the joints of one or more paws at around 4-6 weeks after the initial immunization.

Clinical Evaluation

Mice were examined daily beginning on the day of reimmunization for the appearance of JI. The presence of JI was determined by examining, measuring and scoring each of the forepaws and hindpaws. Collagen induced JI (CIJI) is characterized by swelling and erythema or visible joint distortion of one or more extremities. The severity of JI in each affected paw was scored as: 0—normal joint; 1—visible redness and swelling; 2—severe redness and swelling affecting entire paw or joint; or 3—deformed paw or joint with ankylosis. The sum of the scores for all four paws in each mouse was used as an index (the "JI index") to assess overall disease severity and progression.

Anti-Complement Monoclonal Antibodies

Monoclonal antibodies that bind to and block mouse C5 were prepared by standard methods from hybridoma BB5.1 (Frei, et al., 1987), which was obtained from Dr. Brigitta Stockinger of the National Institute for Medical Research, Mill Hill, London, England. Anti-human C8 hybridoma, 135.8, which generates an Mab that does not block mouse C8, was obtained from Dr. Peter Sims (Blood Research Institute, Milwaukee, Wis.). Both antibodies are IgG1isotypes, and ascites of BB5.1 or 135.8 were obtained in athymic nude mice or BALB/c mice, respectively. IgGs were purified from ascites with a protein A affinity collum eluted with acetic acid, and subsequently dialyzed against PBS. Purified antibodies were quantified by spectrophotometric determination of absorbance at 280 nm and sterilized with a 0.22 μm filter.

Antibody Administration

For prophylactic treatment, mice were randomly divided as C5 blocker treated and control treated groups and subsequently received 750 μg per mouse ip doses of either anti-mouse C5 mAb, BB5.1, or anti-human C8 mAb, 135.8, as a control, twice weekly. For therapeutic treatment of established JI, mice received anti-mouse C5 mAb BB5.1 or anti-human C8 mAb 135.8 at 2-5 mg/mouse ip daily for 10 days after the initial onset of JI was observed. The doses of anti-C5 mAb were adjusted in a range spanning 2 mg to 5 mg per injection to ensure that the desired depletion of C5 mediated hemolytic activity was obtained, i.e., a depletion of at least 50%.

Unlike the situation in humans, where administration of a C5 blocker to a body fluid of genetically unrelated individuals results in roughly equivalent levels of complement inhibition, the dose of anti-murine-C5 mAb required to deplete hemolytic activity by a given amount in mice is strain dependent. The dose required to deplete hemolytic activity in DBA/1LacJ mice is approximately four times higher than the dose required to achieve an equivalent depletion of the hemolytic activity in BALB/c mice.

T Cell Stimulation Assays

Lymph node cells taken from animals at the time of sacrifice were analyzed for specific T cell responses to collagen II. T cells ($5 \times 10^5$) were incubated with $5 \times 10^5$ mitomycin C (50 μg/ml) treated syngeneic spleen cells from normal DBA/1LacJ mice in flat bottomed 96-well plates. Bovine collagen II (B-CII), bovine CI (B-CI), chicken CII (C-CII) and ovalbumin or BSA were added to cultures at 20 μg/ml. The culture medium was RPMI-1640 supplemented with 5% heated inactivated FCS, $5 \times 10^{-5}$ M 2-ME, 10 mM HEPES buffer, 1% L-glutamine, 1% sodium pyruvate, and 1% penstrep. The cultures were incubated at 37° C. in 5% $CO_2$ for 4 days. Eighteen hours before harvesting, 1 μci of $^3$H-thymidine was added to each well. Results are expressed as cpm obtained from triplicate T cell cultures.

Quantification of Anti B-CII Antibodies

Mice were bled at various times after immunization with B-CII. Serum anti B-CII antibody titers were measured using a conventional ELISA for B-CII similar to the ELISA for anti C5 antibodies described below in Example 8, but using B-CII to coat the plates (also see Myers,. et al., 1989, and Seki et al., 1992, for descriptions of similar assays).

Histological Examination

Mice from each group were sacrificed and all four legs from each mouse were fixed in 10% buffered formalin and decalcified in a solution of 3.1% HCL, 5% formic acid and 7% aluminum chloride. The tissue samples were embedded in paraffin, sectioned at 5 μm and stained with hematoxylin and eosin. For immunofluorescence staining, paws were decalcified in a 0.1M Tris solution containing 10% EDTA and 7.5% PVP for 3 days and frozen in OCT at −80° C. 5 μm sections were then prepared and stained with 9FITC conjugated goat anti-mouse IgG, IgA, and IgM (Zymed Laboratories, South San Francisco, Calif., Catalog No. 65-6411) at a dilution of 1 to 50.

EXAMPLE 1

Therapeutic Effects of C5 Blocker Treatment after the Clinical Onset of Collagen Induced Joint Inflammation In order to assess the effects of administration of a C5 blocker on established JI, mice were observed following induction of CIJI, as described above, and pairs of mice were selected that showed the initial appearance of readily detectable JI symptoms (swollen joints of the paws) on the same day. One mouse of each such pair was treated with a anti-C5 mAb BB5.1 and one was treated with a control injection of either the irrelevant mAb 135.8 or PBS. In each matched pair, the animal with the greatest overall level of paw inflammation was assigned to the C5 blocker treatment group so as to avoid potentially biasing the results in favor of the C5 blocker treatment. Starting on the first day when joint inflammation was observed as paw inflammation, treatments were continued daily for 10 days. (In one case a pair of mice was only carried for 8 days.) In addition to these matched pairs, two unpaired animals also received the C5 blocker treatment after the induction of JI.

Figure 1B:
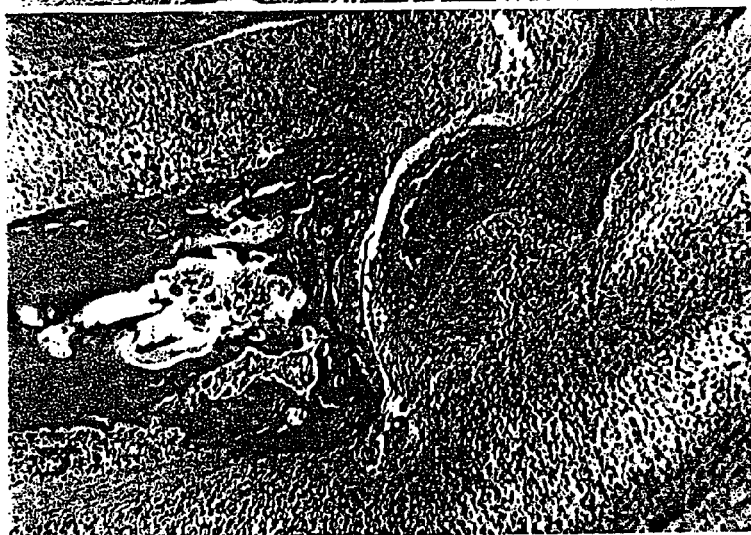
Figure 1C:

Histological examination of initially affected joints from control-treated mice at the end of the treatment period revealed extensive bone erosion with severe inflammatory cell infiltration, thickening of the synovial membranes, and pannus formation (FIG. 1b). In contrast, the initially affected joints of the C5 blocker treated group showed preserved joint structure with some degree of thickening of synovial membranes and mononuclear cell infiltration into some of the joints (FIG. 1c). The severe inflammatory cell infiltration in the control-treated joints was predominantly made up of polymorphonuclear cells (PMNs, neutrophils). Surprisingly, such PMN infiltration was almost completely absent in the C5 blocker treated mice.

During the clinical course of CIJI, an important indicator of the progression of disease is the involvement of additional limbs. Therefore, the number of limbs with clinically detectable JI at the end of the treatment period was compared with the number of limbs exhibiting JI symptoms before the start of therapy. The severity and progression of JI in each affected paw was determined and scored as described above under the heading "Materials and Methods", and the sum of the scores for all four paws of each animal was used as a "JI index". The thicknesses of all four paws of each animal were also measured with a caliper during the time of this experiment to provide a completely objective evaluation of this aspect of disease progression.

Figure 2A:
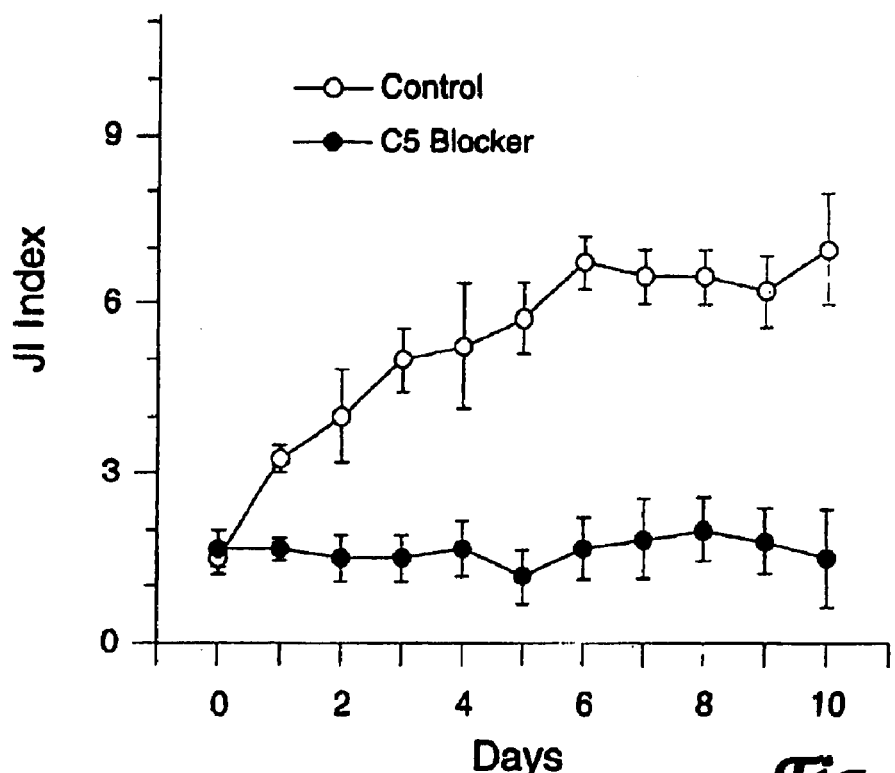
FIGS. 2*a-b* are plots demonstrating the ability of a C5 blocker to stop the progression of pathology of an inflamed joint.

As shown in Table 1 (mean values) and Table 2 (individual values), there were significant increases in new limb involvement in the control treated group during the course of 10 day treatment, while the number of inflamed limbs was decreased when DBA/1LacJ mice with inflamed joints were treated with the C5 blocker starting at the time of disease onset. In addition to new limb recruitment, the initially affected paws of the control treated animals evidenced progression of inflammatory joint disease severity by becoming more inflamed (FIG. 2a). Acute inflammation in the affected joints was observed as severe joint swelling and redness during the first few days, followed by joint deformation and ankylosis at the end of 10 day period. In contrast, no new paws were involved and the severity of inflammation in the majority of affected joints subsided or remained unchanged during the course of C5 blocker therapy (FIG. 2a).

Figure 2B:
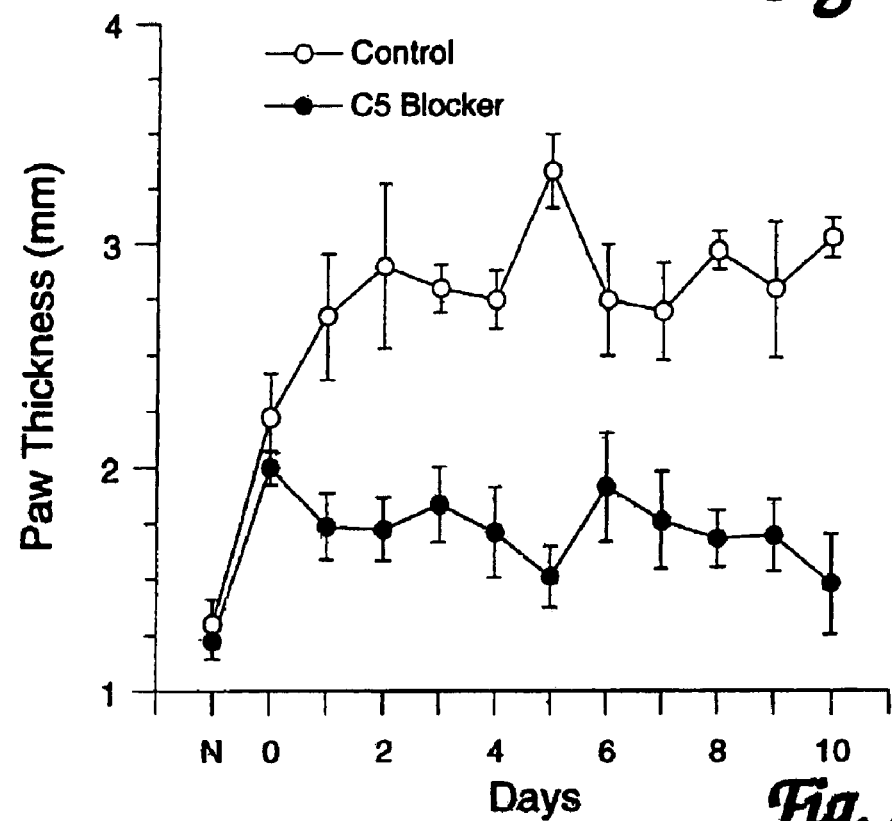
Figure 3A:
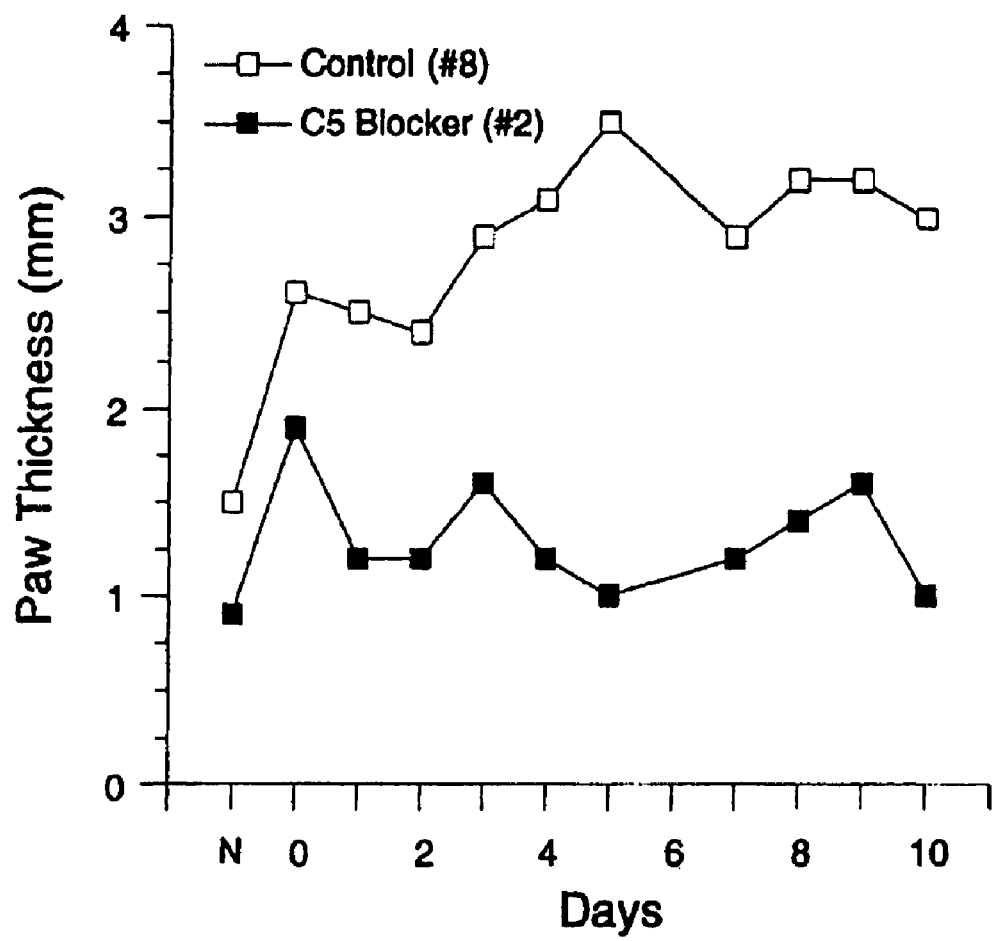
FIGS. 3*a-e* are plots of paw thickness versus time for C5 blocker treated and control treated mice.
Figure 3B:
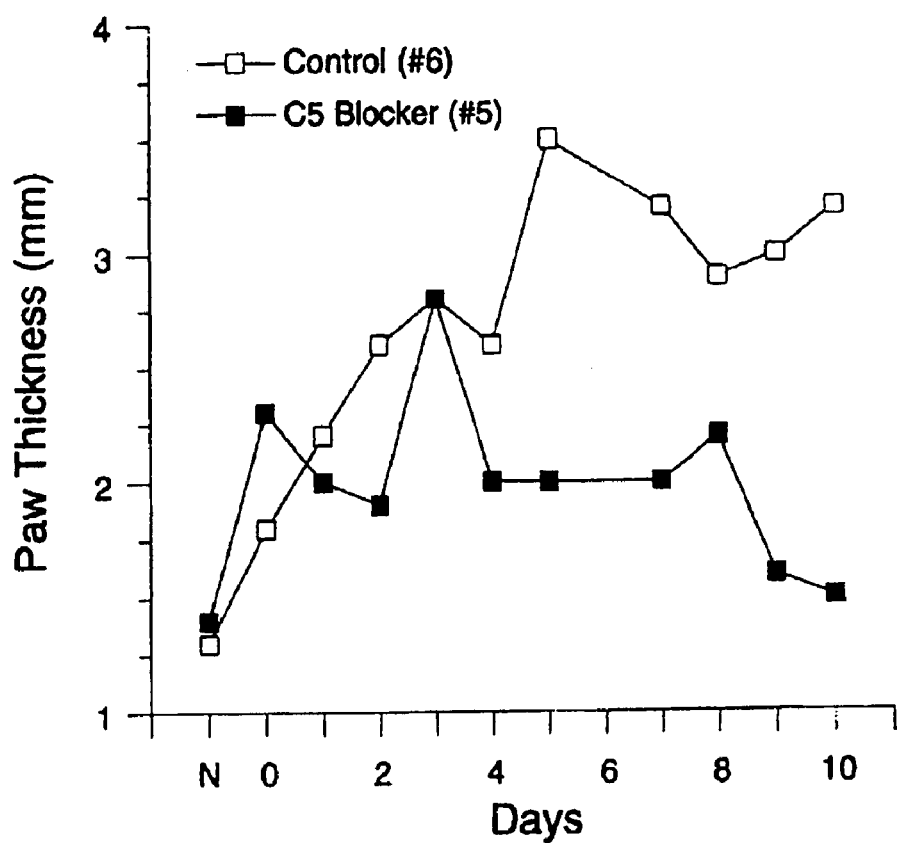
Figure 3C:
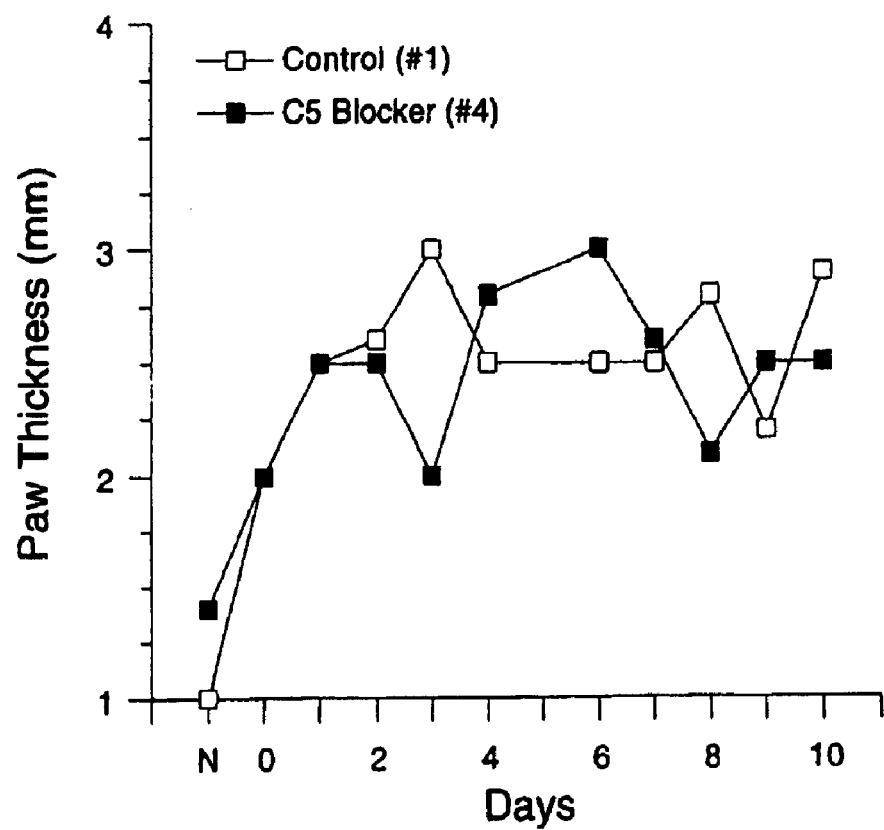
Figure 3D:
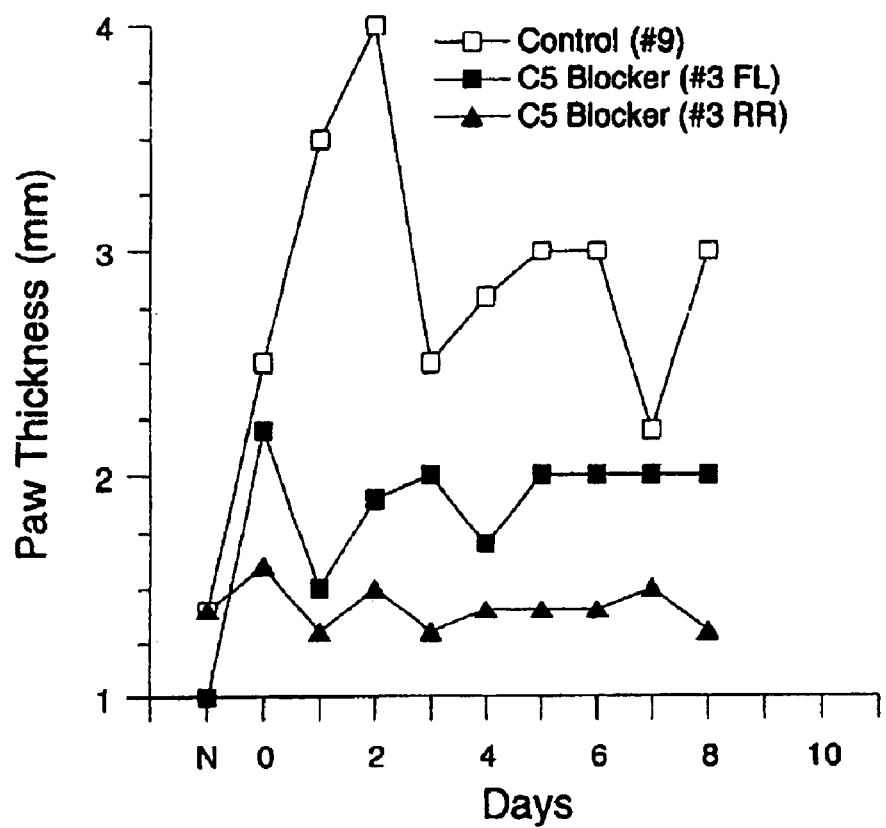
Figure 3E:
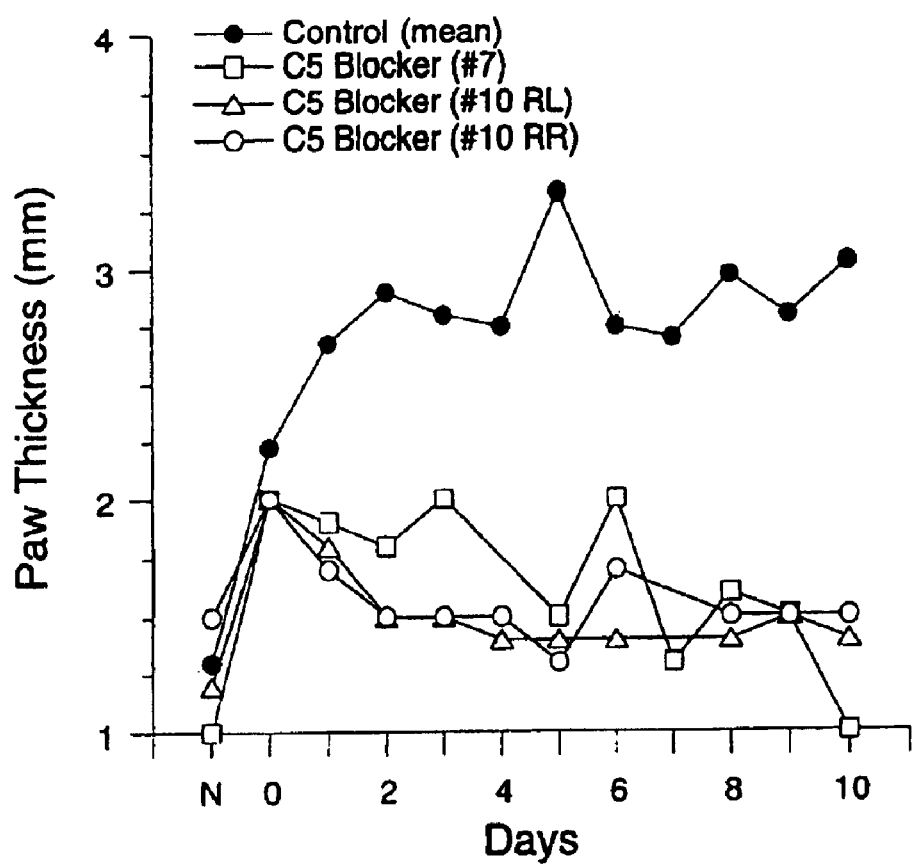

The paw thicknesses of initially affected limbs in both C5 blocker treated and control treated groups during the course of these experiments is shown as mean values for each group in FIG. 2b. FIGS. 3a, 3b, 3c, and 3d show values for each initially inflamed paw of each of the matched pairs of control treated and C5 blocker treated animals, while FIG. 3e shows the values obtained for each initially inflamed paw of each of the unpaired C5 blocker treated animals (shown along with the mean values for control treated animals of FIG. 2b). In these figures, the number in parenthesis indicates the designation of the particular animal, while the letters following the numbers (only in those cases where more than one limb was affected initially) indicate the particular paws affected, with the first letter indicating front (F) or rear (R) paws, and the second letter indicating right (R) or left (L) paws.

As can be seen in FIGS. 2 and 3, and in Tables 1 and 2, C5 blocker treatment successfully prevented further paw recruitment and reduced (but did not completely abolish) the inflammation in the initially affected joints in all but one (mouse #4) of the C5 blocker treated animals. As can be seen in FIG. 2b, the mean thickness of initially affected paws in the control treated group increased significantly during the 10 day period, while the mean thickness of initially affected paws in the C5 blocker treated group decreased, but not significantly.

EXAMPLE 2

Prophylactic Treatment with a C5 Blocker Prevents Collagen Induced Joint Inflammation In these experiments, the administration of the C5 blocker coincided with the reimmunization of the experimental animals with B-CII. On the day of reimmunization, mice were symptom free, and were randomly assigned to C5 blocker treatment or control treatment groups. Each mouse was treated with either the C5 blocker (anti-mouse C5 mAb, BB5.1) or a control treatment (anti-human C8 mAb, 135.8) at 750 μg per mouse ip twice weekly. The animals were treated for four weeks, at which time treatment was discontinued. The results of this study are shown in FIGS. 4 and 5.

Figure 5A:
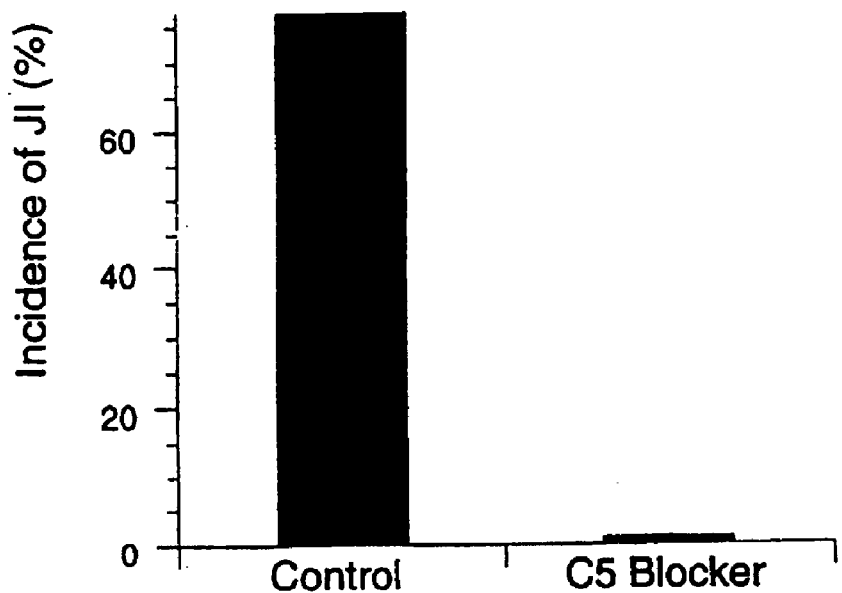
FIG. 5*a* is a comparison of the incidence of Collagen-Induced joint inflammation in C5 blocker treated mice (n=9) and in a pool of mice treated with two different control treatments (n=10). The data represent the overall (total) incidence of joint inflammation seen within two months after the initiation of treatment.
Figure 5B:
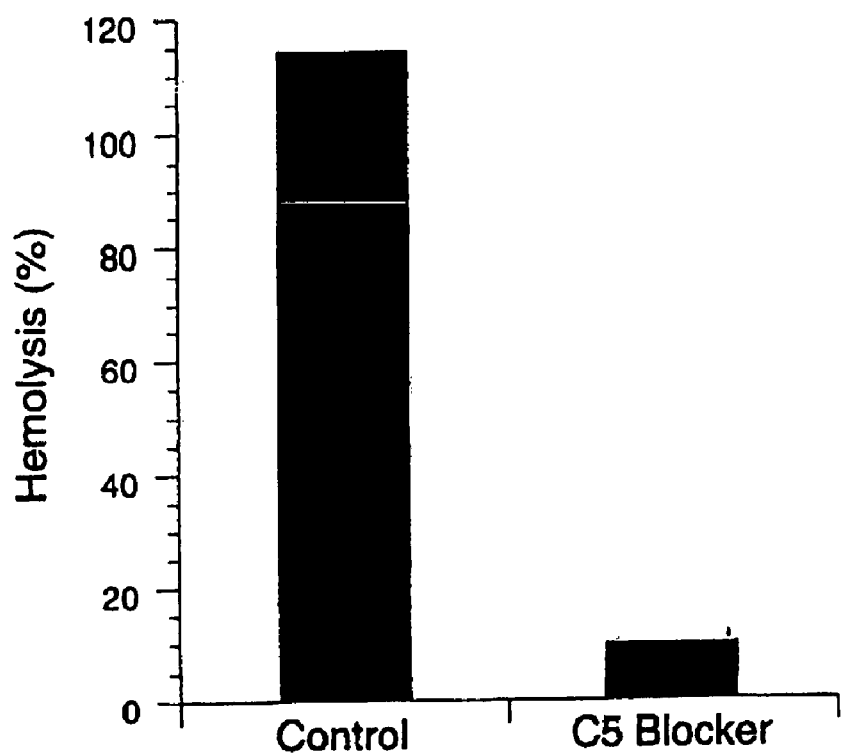
FIG. 5*b* is a comparison of serum hemolytic activity of C5 blocker treated mice (n=5) and control treated mice (n=3) two weeks after the initiation of treatment.

Administration the C5 blocker completely prevented the development of CIJI (0/8). All mice in the C5 blocker treated group exhibited no signs of clinical disease during the period of treatment (and for up to two months after discontinuing the C5 blocker therapy in the two animals followed for that long). In contrast, 90% of the control treated animals (9/10) developed JI by 4-6 weeks after the first B-CII immunization. The percent incidence of JI observed in the control treated and C5 blocker treated animals after 4-6 weeks is plotted in FIG. 5a. (Note that the value for the C5 blocker treated group in this figure is actually 0%, but a bar indicating 1% has been plotted in order to indicate that the data for this set of animals was obtained and is presented.) Peak inflammation levels were observed around 5 weeks after the initial collagen immunization. As shown in FIG. 5b, 80% to 90% of the serum hemolytic activity was depleted in the C5 blocker treated group, while the serum hemolytic activity remained normal in the control treated group.

Figure 4A:
FIGS. 4*a-c* are photomicrographs of joints stained with Hematoxylin and Eosin illustrating the use of a C5 blocker to prevent the onset of joint inflammation.
Figure 4B:
Figure 4C:

As shown in FIG. 4, histological examination of affected joints from control mice revealed extensive mononuclear cell as well as polymorphonuclear cell infiltration, thickening of the synovial membrane and bone erosion by the expanding synovial pannus (FIG. 4b). In contrast, there were no signs of inflammatory processes observed in the majority of joints studied from the C5 blocker treated mice. A few joints from these C5 blocker treated mice showed some subclinical thickening of the synovial membrane, but this alteration was not accompanied by any visible bone erosion or inflammatory cell infiltration (FIG. 4c). Interestingly, immunofluorescence staining showed antibody deposition along cartilage surfaces and C3 activation at synovial membranes in the joints of both the control treated and the C5 blocker treated animals.

EXAMPLE 3

Figure 6A:
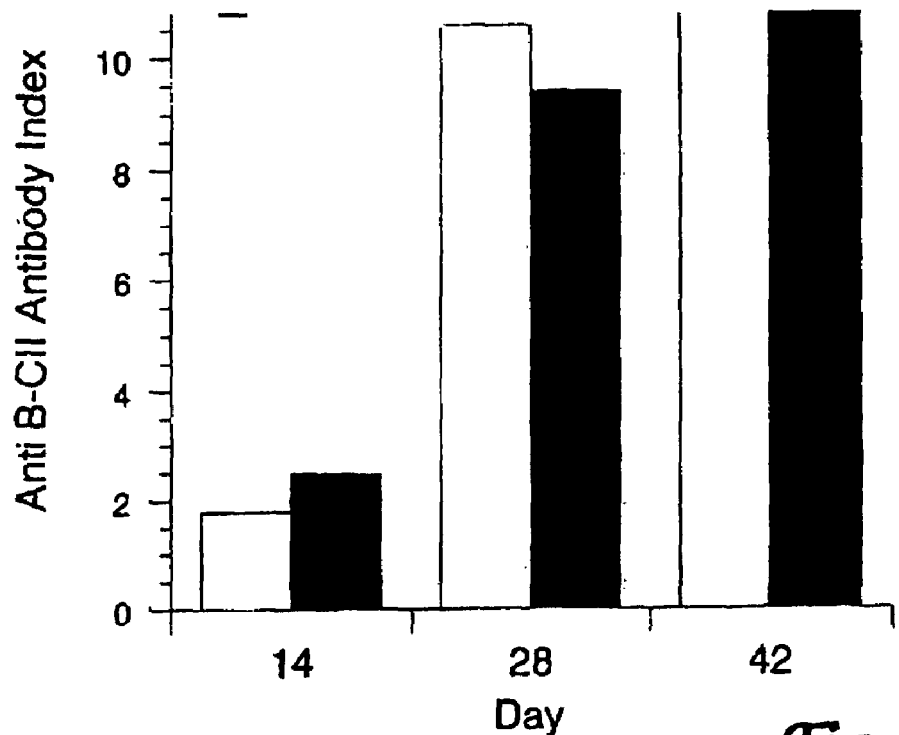
FIG. 6a was prepared by analyzing serum samples obtained from C5 blocker treated (n=4) or control treated mice (n=4) at the indicated time after CII immunization. The samples were analyzed for anti B-CII IgG in an ELISA assay. The anti B-CII antibody index represents the ratio of optical densities obtained from positive serum and negative sera.

Effect of C5 Blocker Treatment on the Humoral and Cellular Immune Responses to Immunization with Collagen Responses of both the humoral and cellular immune systems are activated after immunization of DBA/1LacJ mice with bovine Collagen II. Anti B-CII titers increase, and the serum IgG anti B-CII titers in C5 blocker treated mice are equivalent to those of control treated mice when tested at 14, 28 and 42 days after the initial B-CII immunization (FIG. 6a). Anti B-CII antibody titers from both control and anti-C5 mAb treated mice rise significantly after the B-CII reimmunization and remain at the resulting plateau for an extended period of time.

Figure 6B:
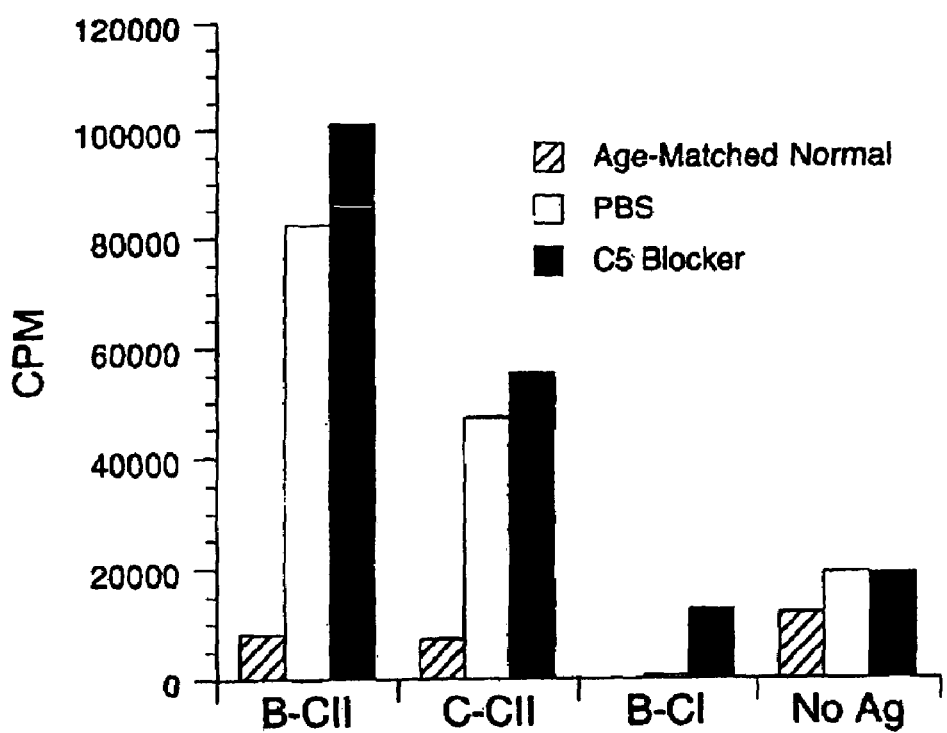
FIG. 6b was prepared by culturing lymph node T cells ($5 \times 10^5$) in vitro with 20 µg/ml B-CII, C-CII, B-CI or medium only, in the presence of $5 \times 10^5$ of mitomycin C treated syngeneic spleen cells for a total of 4 days, following which the cells were pulsed with $^3$H-thymidine, 18 hours before harvest.

In order to study T cell responses, lymph node cells (LNCs) from C5 blocker treated mice and control treated mice were cultured with either B-CII, B-CI, C-CII, or culture medium only. LNCs from either C5 blocker treated mice or control treated mice responded specifically and equally to B-CII regardless of the treatment the animals received concurrently with B-CII reimmunization. C-CII, which shares many conserved regions of homology with B-CII also elicited a moderate T cell response when cultured with LNCs from C5 blocker treated mice or from control treated mice. In contrast, LNCs from age matched non-immunized mice responded poorly to all of the tested collagens (FIG. 6b).

The data obtained in these experiments and those of Examples 1 and 2 clearly demonstrate that in vivo administration of a C5 blocker prevents the development and progression of CIJI and that this treatment does not interfere with the humoral and cellular immune responses seen after immunizing mice with bovine type II collagen. Both collagen-specific T cell responses and anti-CII antibody titers were comparable in both the C5 blocker treated mice and the control treated B-CII reiunmunized mice.

EXAMPLE 4

C5 Blocker Inhibition of Complement Activity

The effects of a C5 blocker on complement activation were evaluated using a closed-loop cardio-pulmonary bypass (CPB) model for the extracorporeal circulation of human blood. As discussed fully in copending U.S. patent application Ser. No. 08/217,391, filed Mar. 23, 1994, extracorporeal circulation of human blood causes activation of complement in the blood.

The C5 blocker was a monoclonal antibody raised in mice against purified human C5 protein (Wurzner, et al., *Complement Inflamm* 8:328-340, 1991; mAb N19-8) that was propagated, recovered and purified as an IgG fraction from mouse ascites fluid (*Antibodies, A Laboratory Manual*, Cold Spring Harbor Laboratory, New York, 1988; *Current Protocols In Immunology*, John Wiley & Sons, New York, 1992).

To carry out these experiments, 300 ml of whole human blood was drawn from a healthy human donor and additionally a 1 ml sample was removed as a control sample for later analysis. The blood was diluted to 600 ml by the addition of Ringer's lactate solution containing 10 U/ml heparin. The C5 blocker (30 mg in sterile PBS) was added to the diluted blood to a final concentration of 50 µg/ml. In a control experiment, an equal volume of sterile PBS was added to the diluted blood. The blood was then used to prime the extracorporeal circuit of a COBE CML EXCEL membrane oxygenator CPB machine (Cobe BCT, Inc., Lakewood, Colo.) and the circuit was started. The circuit was cooled to 28° C. and circulated for 60 minutes. The circuit was then warmed to 37° C. and circulated for an additional 30 minutes. The experiment was then terminated. Samples were taken at several time points and evaluated for complement activity (FIG. 7).

At each time point an aliquot of whole blood was taken, divided into 3 samples and A) diluted 1:1 in 2% paraformaldehyde in PBS to evaluate platelet and blood cell activation parameters as discussed in the above-referenced U.S. patent application Ser. No. 08/217,391; B) centrifuged to remove all cells and plasma diluted 1:1 in Quidel sample preservation solution (Quidel Corporation, San Diego, Calif.) and stored at −80° C., following which these frozen diluted plasma samples were thawed and used to evaluate C3a and C5b-9 generation (Examples 5 and 6, respectively), and C) centrifuged to remove all cells and undiluted plasma stored at −80° C., following which these frozen plasma samples were thawed and hemolytic assays were performed as described above.

Figure 7:
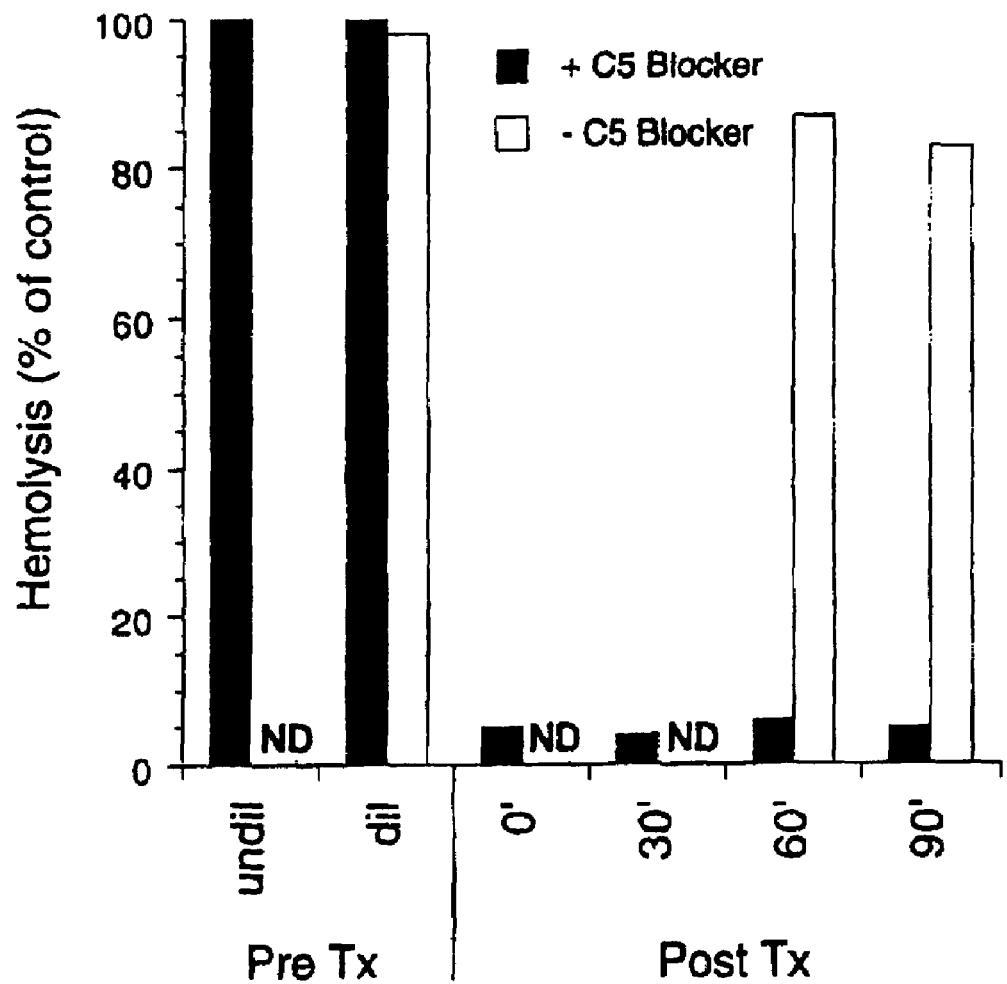
FIG. 7 shows the results of hemolytic assays demonstrating inhibition of complement activity associated with human blood circulated through an extracorporeal circuit following treatment with a C5 blocker. Assays were performed before the addition of the blocker or the commencement of the CPB circuit ("Pre Tx") using undiluted blood ("undil") and diluted blood ("dil") as described in Example 4. Samples of diluted blood to which the blocker had been added ("Post Tx") were assayed at the times indicated after starting the CPB circuit.

As can be seen in FIG. 7, addition of the C5 blocker to the extracorporeal circuit resulted in a 95% reduction of the cell-lysing ability of complement in the plasma. The complement activity remained inhibited throughout the course (90 minutes) of the experiment.

EXAMPLE 5

Generation of C3a in the Presence of a C5 Blocker

The fresh frozen plasma samples that had previously been diluted in Quidel sample preservation solution following CPB circulation (see Example 4) were assayed for the presence of the complement split product C3a by using the Quidel C3a EIA kit (Quidel Corporation, San Diego, Calif.). These measurements were carried out according to the manufacturer's specifications. C3a released is expressed in ng/well as determined by comparison to a standard curve generated from samples containing known amounts of human C3a.

Figure 8:
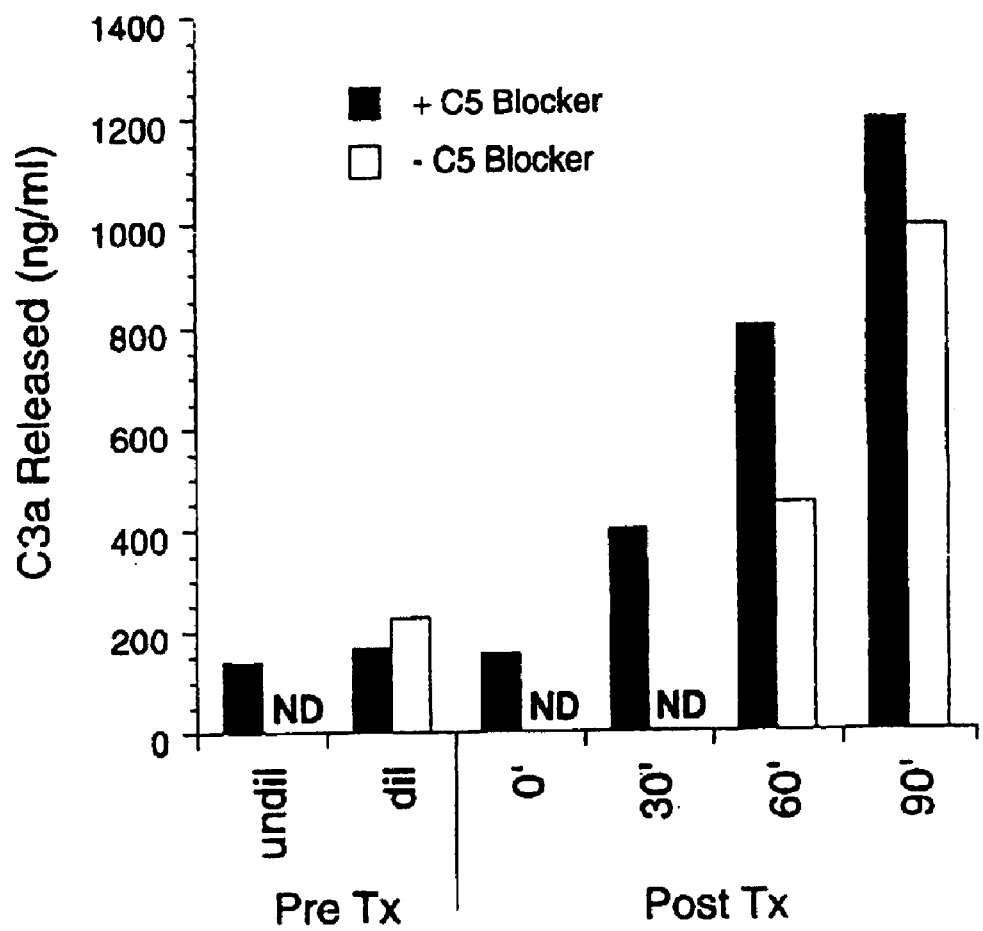
FIG. 8 shows the results of assays of levels of complement component C3a demonstrating that the generation of complement component C3a in whole human blood circulated through an extracorporeal circuit is not inhibited by the addition of a C5 blocker to such whole blood. Assays were performed before the addition of the blocker or the commencement of the CPB circuit ("Pre Tx") using undiluted blood ("undil") and diluted blood ("dil") as described in Example 5. Samples of diluted blood to which the blocker had been added ("Post Tx") were assayed at the times indicated after starting the CPB circuit.

As seen in FIG. 8, addition of the C5 blocker had no effect on the production of C3a during the CPB experiment. C3a generation was dramatically increased during the final 30 min. of the experiment and correlates with sample warming.

EXAMPLE 6

Prevention of the Generation of C5b-9 by a C5 Blocker

Fresh frozen plasma samples that had been previously diluted in Quidel sample preservation solution following CPB circulation (see Example 4) were assayed for the presence of the terminal human complement complex C5b-9 using the Quidel C5b-9 kit (Quidel Corporation, San Diego, Calif.). The amount of soluble C5b-9 (sC5b-9) in each sample was determined using the manufacturers specifications and is expressed in arbitrary absorbance units (AU).

Figure 9:
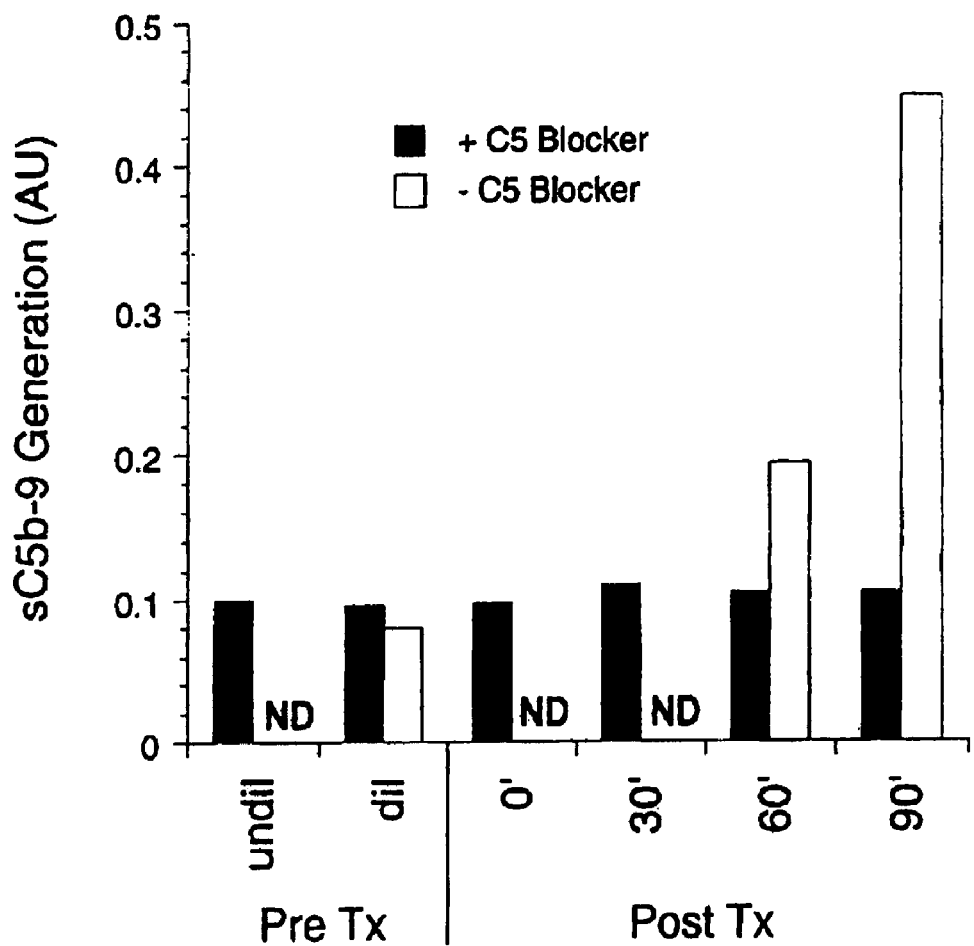
FIG. 9 shows the results of assays of the levels of soluble C5b-9 (sC5b-9) in human blood circulated through an extracorporeal circuit demonstrating that the addition of a C5 blocker to such whole blood inhibits the formation of the C5b-9 terminal complement assembly. Assays were performed before the addition of the blocker or the commencement of the CPB circuit ("Pre Tx") using undiluted blood ("undil") and diluted blood ("dil") as described in Example 6. Samples of diluted blood to which the blocker had been added ("Post Tx") were assayed at the times indicated after starting the CPB circuit.

As can be seen in FIG. 9, the C5 blocker completely inhibited C5b-9 generation during extracorporeal circulation so that sC5b-9 levels during the full course of the run were equivalent to control ($t_0$) time points. The results of this experiment and those of Examples 4 and 5 show that the addition of a C5 blocker to human blood undergoing extracorporeal circulation effectively inhibits both complement hemolytic activity (FIG. 7) and C5b-9 generation (FIG. 9), but not C3a generation (FIG. 8).

EXAMPLE 7

Pharmacokinetics of mAb C5 Blockers

The in vivo duration of action of mAb BB5.1, and a Fab' fragment of mAb BB5.1 (prepared by standard methods) was determined in normal female BALB/cByJ mice (averaging approximately 20 gms each) which were obtained from the Jackson Laboratory, Bar Harbor, Me. The mice were given a single intravenous injection (at 35 mg/kg body weight) of the mAb or the Fab' fragment of the mAb (or an equal volume of PBS as a control). Blood samples were collected from the retroorbital plexus at 1, 4, 24, 96, and 144 hours after administration of PBS; 4, 16, and 24 hours after administration of the Fab' fragment of mAb BB5.1; and 4, 24, 48, 72, 96, and 144 hours after administration of intact mAb BB5.1.

Figure 10A:
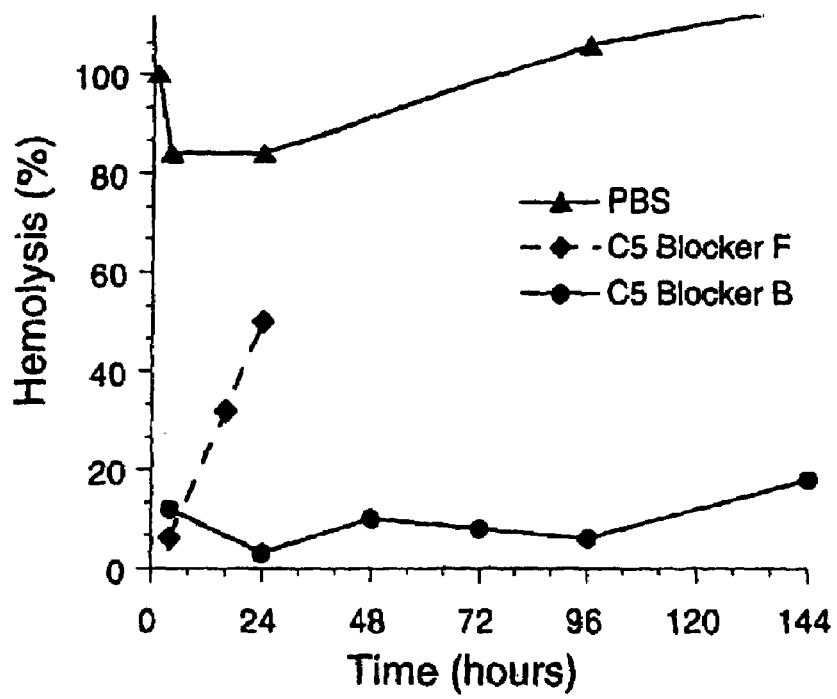
FIGS. 10a-b show pharmacokinetic analyses of the reduction of the cell lysis ability of mouse blood (FIG. 10a) or extracorporeally circulating human blood (FIG. 10b) after treatment with various C5 blockers. C5 Blocker B is monoclonal antibody BB5.1; C5 Blocker F is an Fab' fragment of monoclonal antibody BB5.1; C5 Blocker N is monoclonal antibody N19-8.

FIG. 10a shows the time course of inhibition of the cell-lysing ability of complement in mouse blood (determined by testing serum obtained from the blood and diluted to 2.5% in hemolytic assays, as described above) after the in vivo administration of the intact mAb, the Fab' fragment, or the PBS. As shown in the figure, the intact mAb almost completely inhibited the hemolytic activity of the blood throughout the 6 day test period. The Fab', however, had a half-life of approximately 24 hours.

In addition to the above experiments, at the end of the 6 day testing period all of the mice were sacrificed. Kidneys, lungs, and livers were harvested and examined by gross inspection, as well as by microscopic examination of stained sections. All of the organs of the C5 blocker treated animals appeared the same as those taken from the PBS control treated animals. The overall appearance of these test and control mice was also indistinguishable prior to necropsy.

Figure 10B:
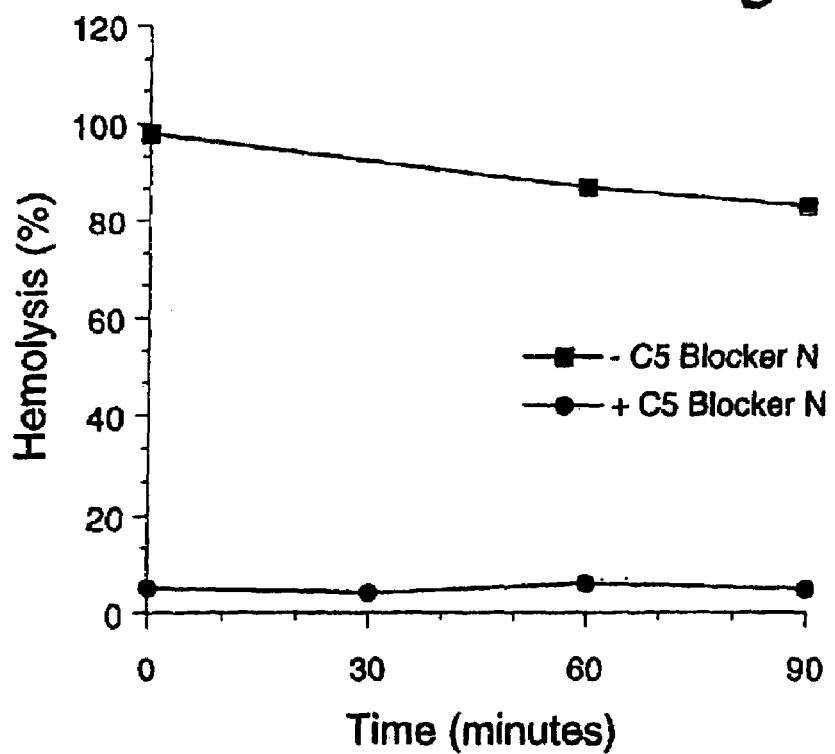

An anti-human C5 mAb was also tested for pharmacokinetic properties in circulating human blood as described above in Example 4. As described therein, the hemolysis-inhibiting effects of this C5 blocker were assayed over a 90 minute period of circulation. The results of these assays are charted in FIG. 10$b$, and show that the C5 blocker essentially completely inhibited the cell lysing ability of the human blood during the entire 90 minute period of circulation.

The results of these experiments demonstrate that these C5 blockers will survive in the bloodstream for a substantial period of time, thus making periodic administration practical.

EXAMPLE 8

Preparation of a C5 Blocker

A C5 blocker mAb suitable for use in the practice of the present invention, was prepared as follows.

Balb/c mice were immunized three times by intraperitoneal injection with human C5 protein (Quidel Corporation, San Diego, Calif., Catalog #A403). The first injection contained 100 μg of C5 protein in a complete Freund's adjuvant emulsion, the second immunization contained 100 μg of C5 protein in an incomplete Freund's adjuvant emulsion, and the third immunization was 100 μg of protein in PBS. The mice were injected at roughly 2 month intervals.

Fusions of splenocytes to myeloma cells to generate hybridomas were performed essentially as described in Current Protocols in Immunology (John Wiley & Sons, New York, 1992, pages 2.5.1 to 2.5.17). One day prior to fusion the mice were boosted IV with 100 μg of C5 protein. On the day of fusion, the immunized mice were sacrificed and spleens was harvested. SP2/0-AG14 myeloma cells (ATCC CRL#1581) were used as the fusion partner. SP2/0-AG14 cultures were split on the day before the fusion to induce active cell division. A ratio of 1:10 (myeloma cells:splenocytes) was used in the fusions.

The cells were fused using PEG 1450 in PBS without calcium (Sigma Chemical Company, St. Louis, Mo., Catalog No. P-7181) and plated at 1-2.5×10$^5$ cells per well. Selection in EX-CELL 300 medium (JRH Biosciences, Lexena, Kans., Catalog No. 14337-78P) supplemented with 10% heat inactivated fetal bovine serum (FBS); glutamine, penicillin and streptomycin (GPS); and HAT (Sigma Chemical Company, St. Louis, Mo., Catalog No. H-0262) was started the following day. The fusions were then fed every other day with fresh FBS, GPS, and HAT supplemented medium. Cell death could be seen as early as 2 days and viable cell clusters could be seen as early as 5 days after initiating selection. After two weeks of selection in HAT, surviving hybridomas chosen for further study were transferred to EX-CELL 300 medium supplemented with FBS, GPS, and HT (Sigma Chemical Company, St. Louis, Mo., Catalog No. H-0137) for 1 week and then cultured in EX-CELL 300 medium supplemented with FBS and GPS.

Hybridomas were screened for reactivity to C5 and inhibition of complement-mediated hemolysis 10-14 days after fusion, and were carried at least until the screening results were analyzed. The screen for inhibition of hemolysis was the chicken erythrocyte lysis assay described above. The screen for C5 reactivity was an ELISA, which was carried out using the following protocol.

A 50 μL aliquot of a 2 μg/ml solution of C5 (Quidel Corporation, San Diego, Calif.) in sodium carbonate/bicarbonate buffer, pH 9.5, was incubated overnight at 4° C. in each test well of a 96 well plate (Nunc-Immuno F96 Polysorp, A/S Nunc, Roskilde, Denmark). The wells were then subjected to a wash step. (Each wash step consisted of three washes with TBST.) Next, test wells were blocked with 200 μL of blocking solution, 1% BSA in TBS (BSA/TBS), for 1 hour at 37° C. After an additional wash step, a 50 μL aliquot of hybridoma supernatant was incubated in each test well for 1 hour at 37° C. with a subsequent wash step. As a secondary (detection) antibody, 50 μL of a 1:2000 dilution of horseradish peroxidase (HRP) conjugated goat anti-mouse IgG in BSA/TBS, was incubated in each test well for 1 hour at 37° C., followed by a wash step. Following the manufacturer's procedures, 10 mg of O-phenylenediamine (Sigma Chemical Company, St. Louis, Mo., Catalog No. P-8287) was dissolved in 25 mLs of phosphate-citrate buffer (Sigma Chemical Company, St. Louis, Mo., Catalog No. P-4922), and 50 μL of this substrate solution was added to each well to allow detection of peroxidase activity. Finally, to stop the peroxidase detection reaction, a 50 μL aliquot of 3N hydrochloric acid was added to each well. The presence of antibodies reactive with C5 in the hybridoma supernatants was read out by a spectrophotometric OD determination at 490 nm.

The supernatant from a hybridoma designated as 5G1.1 tested positive by ELISA and substantially reduced the cell-lysing ability of complement present in normal human blood in the chicken erythrocyte hemolysis assay. Further analyses revealed that the 5G1.1 antibody reduces the cell-lysing ability of complement present in normal human blood so efficiently that, even when present at roughly one-half the molar concentration of human C5 in the hemolytic assay, it can almost completely neutralize serum hemolytic activity.

Hybridoma 5G1.1 was deposited with the American Type Culture Collection, 12301 Parklawn Drive, Rockville, Md. 20852, United States of America, on Apr. 27, 1994, and has been assigned the designation HB-11625. This deposit were made under the Budapest Treaty on the International Recognition of the Deposit of Micro-organisms for the Purposes of Patent Procedure (1977).

Throughout this application various publications and patent disclosures are referred to. The teachings and disclosures thereof, in their entireties, are hereby incorporated by reference into this application to more fully describe the state of the art to which the present invention pertains.

Although preferred and other embodiments of the invention have been described herein, further embodiments may be perceived by those skilled in the art without departing from the scope of the invention as defined by the following claims.

REFERENCES

Abbink et al., 1992. *Annals Rheumatic Dis* 51, pp. 1123-1128.
Andersson and Holmdahl, 1990. *Eur J Immunol* 20, pp. 1061-1066.
Andersson et al., 1991. *Immunology* 73, pp. 191-196.
Andersson et al., 1992. *Immunogenetics* 35, pp. 71-72.
Arnett, 1992. *Cecil Textbook of Medicine*, Wyngaarden et al. (editors). W. B. Saunders Company, Philadelphia, Chapter 258, pp. 1508-1515.
Auda et al., 1990. *Rheumatol Int* 10, pp. 185-189.
Banerjee et al., 1988A. *J Immunol* 141, pp. 1150-1154.
Banerjee et al., 1988B. *J Exp Med* 167, pp. 832-839.
Banerjee et al., 1989. *J Immunol* 142, pp. 2237-2243.
Boissier et al., 1987. *Annals Rheumatic Dis* 46, pp. 691-700.
Brahn and Trentham, 1989. *Cell Immunol* 118, pp. 491-503.
Brodeur et al., 1991. *Arthr Rheumat* 34(12), pp. 1531-1537.
Cannon et al., 1990. *Agents and Actions* 29, pp. 315-323.
Cash and Klippel, 1994. *New England J Med* 330, pp. 1368-1375.
Chiocchia et al., 1990. *J Immunol* 145, pp. 519-525.
Chiocchia et al., 1991. *Eur J Immunol* 21, pp. 2899-2905.
Clackson et al., 1991. *Nature* 352, pp. 624-628.
Coligan et al. (eds.), 1992. *Current Protocols In Immunology*, John Wiley & Sons, New York.
Corvetta et al., 1992. *Clinic Exp Rheumat* 10, pp. 433-438.
David, 1992. *Immunogenetics* 35, pp. 69-70.
De Clerck et al., 1989. *Clinic Exp Rheumat* 7, pp. 485-492.
*Drug Evaluations, Annual* 1991. American Medical Association, 1990.
Durie et al., 1993. *Science* 261, pp. 1328-1330.
Elliot et al., 1993. *Arthr Rheumat* 36(12), pp. 1681-1690.
Fava et al., 1993. *Clin Exp Immunol* 94, pp. 261-266.
Feldmann et al., 1990. *Annals Rheumat Dis* 49(1), pp. 480-486.
Feldmann et al., 1991. *Immunol Review* 119, pp. 105-123.
Firestein et al., 1991. *Arthr Rheumat* 34(9), pp. 1094-1105.
Fong et al., 1994. *Clin Exp Rheumat* 12(1), pp. 55-58.
Frei et al., 1987. *Mol Cell Probes* 1, pp. 141-149.
Fujimori et al., 1993. *Agents and Actions* 39, pp. 42-48.
Gilman et al. (eds.), 1990. *Goodman and Gilman's The Pharmacological Basis of Therapeutics* 18th Ed. Pergamon Press, Inc., New York.
Goldschmidt et al., 1990. *Immunol* 69, pp. 508-514.
Goldschmidt and Holmdahl, 1991. *Eur J Immunol* 21, pp. 1327-1330.
Griswold et al., 1988. *Arthrit Rheumat* 31(11), pp. 1406-1412.
Haber, 1992. *Immunol Rev* 130, pp. 189-212.
Haqqi et al., 1989. *Immunogenet* 29, pp. 180-185.
Harigai et al., 1993. *Clinic Immunol Immunopathol* 69(1), pp. 83-91.
Harlow and Lane, 1988. *Antibodies, A Laboratory Manual*, Cold Spring Harbor Laboratory, New York.
Heinz et al., 1989. *Molecul Immunol* 26(2), pp. 163-169.
Holmdahl et al., 1985. *Scand J Immunol* 22, pp. 295-306.
Holmdahl et al., 1986. *Arthrit Rheumat* 29(1), pp. 106-113.
Holmdahl et al., 1989. *Clin Exp Rheumat* 7(S-3), pp. 51-55.
Holmdahl et al., 1990. *Scand J Immunol* 31, pp. 147-157.
Hom et al., 1988. *Eur J Immunol* 18, pp. 881-888.
Hom et al., 1991. *Agents and Actions* 33, pp. 300-309.
Hom et al., 1992. *Clinic Immunol Immunopath* 62(1), pp. 56-65.
Hom et al., 1993. *Immunological Investigations* 22(4), pp. 257-265.
Hong et al., 1979. *J Immunol* 122(6), pp. 2418-2423.
Inoue et al., 1993. *Agents and Actions* 39, pp. 187-194.
Jasin, 1989. *Sem Arthrit Rheumat* 18(4), pp. 86-90.
Jose et al., 1990. *Annals Rheumat Dis* 49, pp. 747-752.
Kabat and Mayer, 1961. *Experimental Immunochemistry*, 2nd Ed. Charles C. Thomas, Springfield, Ill., pp. 135-139.
Kahle et al., 1992. *Annals Rheumat Dis* 51(6), pp. 731-734.
Kakimoto et al., 1988. *J Immunol* 140(1), pp. 78-83.
Kakimoto et al., 1992. *Cellular Immunology* 142, pp. 326-337.
Kleinau et al., 1989. *Clin Exp Immunol* 78, pp. 138-142.
Koch et al., 1994. *J Clin Invest* 94, pp. 1012-1018.
Liddell and Cryer, 1991. *A Practical Guide to Monoclonal Antibodies*, John Wiley & Sons, Chichester, West Sussex, England.
Lipsky, 1994. *Harrison's Principles of Internal Medicine*, 13th Ed, Isselbacher et al. (eds). McGraw-Hill, Inc., New York, Chapter 285, pp. 1648-1655.
Maeurer et al., 1992. *Immunobiol* 185, pp. 103-120.
Matsubara et al., 1991. *Am J Pathol* 138(5), pp. 1279-1291.
McCarty and Koopman, 1993. *Arthritis and Allied Conditions*, 12th Ed. Lea and Febiger, Philadelphia.
Moffat et al., 1989. *Clin Exp Immunol* 78, pp. 54-60.
Mollnes et al., 1986. *Arthr Rheumat* 29(6), pp. 715-721.
Mollnes et al., 1988. *Scand J Immunol* 28, pp. 307-312.
Montz et al., 1990. *Cellular Immunol* 127, pp. 337-351.
Mori et al., 1992. *J Exp Med* 176, pp. 381-388.
Morgan et al., 1981. *Arthrit Rheumat* 24(11), pp. 1356-1362.
Morgan et al., 1988. *Clin Exp Immunol* 73, pp. 473-478.
Morrison, 1992. *Annu Rev Immunol* 10, pp. 239-265.
Moxley and Ruddy, 198.5. *Arthr Rheumat* 28(10), pp. 1089-1095.
Muller-Eberhard, 1988. *Ann Rev Biochem* 57, pp. 321-347.
Myers et al., 1989A. *J Immunol* 143(12), pp. 3976-3980.
Myers et al., 1989B. *J Exp Med* 170, pp. 1999-2010.
Myers et al., 1993. *J Immunol* 150(10), pp. 4652-4658.
Nagler-Anderson et al., 1986. *Proc Natl Acad Sci*, USA 83, pp. 7443-7446.
Nakajima et al., 1993. *Clin Exp Immunol* 92, pp. 328-335.
Nishikaku and Koga, 1993. *Immunopharmacology* 25, pp. 65-74.
Oleesky et al., 1991. *Clin Exp Immunol* 84, pp. 250-255.
Olmez et al., 1991. *Scand J Rheumatol* 20, pp. 183-189.
Olsen et al., 1991. *Arthr Rheumat* 34(2), pp. 187-191.
Osman et al., 1993. *J Exp Med* 177, pp. 387-395.
Peake et al., 1989. *Clin Exp Immunol* 78, pp. 49-53.
Peterman et al., 1993. *J Immunol* 151(11), pp. 6546-6558.
*Physicians' Desk Reference* 47th Ed., 1993. Medical Economics Co., Inc., Montvale, N.J.
Piguet et al., 1992. *Immunol* 77, pp. 510-514.
Reichamnn et al., 1988. *Nature* 332, pp. 323-327.
Reife et al., 1991. *Arthr Rheumat* 34, pp. 776-781.
*Remington's Pharmaceutical Sciences* 17th Ed., 1985. Mack Publishing Company, Philadelphia, Pa.
Rodrigues et al., 1993. *J Immunol* 151, pp. 6954-6961.
Roitt et al., 1988. *Essential Immunology*, 6th Ed. Backwell Scientific Publications, Oxford, England.
Saura et al., 1992. *Rheumat* 12, pp. 141-146.
Seki et al., 1988. *J Immunol* 140(5), pp. 1477-1484.
Seki et al., 1992. *J Immunol* 148(10), pp. 3093-3099.
Shingu et al., 1994. *British J Rheumat* 33, pp. 299-301.
Smith et al., 1990. *Int J Immunopharmac* 12(2), pp. 165-173.
Spannaus-Martin et al., 1990. *Am J Path* 137(2), PP. 331-339.
Spinella and Stuart, 1992. *Immunogenetics* 35, pp. 73-74.
Spinella et al., 1991. *Immunogenetics* 34, pp. 23-27.
Terato et al., 1992. *J Immunol* 148(7), pp. 2103-2108.

*The United States Pharmacopeia* 22nd Ed., 1989. Mack Printing Co., Easton, Pa.
Thompson et al., 1988. *Clin Exp Immunol* 72, pp. 20-25.
Thorbecke et al., 1992. *Proc Natl Acad Sci*, USA 89, pp. 7375-7379.
Trentham et al., 1977. *J Exp Med* 146, pp. 857-868.
Trentham et al., 1993. *Science* 261, pp. 1727-1730.
van Lent et al., 1992. *Am J Path* 140, pp. 1451-1461.
Ward and Zvaifler, 1971. *J Clinical Invest* 50, pp. 606-616.
Ward, 1975. *Annals NY Acad Sci* 256, pp. 169-176.
Watson and Townes, 1985. *J Exp Med* 162, pp. 1878-1891.
Watson et al., 1987. *Arthrit Rheumat* 30(4), pp. 460-465.
Williams et al., 1992A. *Clin Exp Immunol* 88, pp. 455-460.
Williams et al., 1992B. *Proc Natl Acad Sci*, USA 89, pp. 9784-9788.
Williams et al., 1994. *Proc Natl Acad Sci*, USA 91, pp. 2762-2766.
Winter and Milstein, 1991. *Nature* 349, pp. 293-299.
Wolos et al., 1993. *J Immunol* 151(1), pp. 526-534.
Wurzner et al., 1991. *Complement Inflamm* 8, pp. 328-340.
Yoo et al., 1988. *J Exp Med* i68, pp. 777-782.
Zvaifler, 1968. *Univ Michigan Med Center J*, pp. 234-237.
Zvaifler, 1969A. *Annals NY Acad Sci* 168(1), pp. 146-160.
Zvaifler, 1969B. *J Clinical Invest* 48, pp. 1532-1542.
Zvaifler, 1974. *Arthr Rheumat* 17(3), pp. 297-305.

TABLE 1

| Treatment | n | NUMBER OF LIMBS AFFECTED PER GROUP* | | % Change | % Hemolytic Activity |
|---|---|---|---|---|---|
| | | Day 0 | Day 10 | | |
| Control | 4 | 4 (1.0) | 9 (2.3) | +125.0 | 95.6 ± 3.8 |
| C5 Blocker | 6 | 8 (1.3) | 7 (1.2) | −12.5 | 13.9 ± 4.7 |

*Numbers in parenthesis represent the average number of affected joints per mouse.

TABLE 2

| Mouse (treatment) | NUMBER OF LIMBS AFFECTED PER MOUSE | | % Change | % Hemolytic Activity |
|---|---|---|---|---|
| | Day 0 | Day 10 | | |
| #8 (control) | 1 (RL) | 2 (RL & RR) | +100 | 91.2 |
| #2 (C5 blocker) | 1 (FL) | 1 (FL)* | 0 | 22.4 |
| #6 (control) | 1 (RR) | 2 (RR & RL) | +100 | 103.2 |
| #5 (C5 blocker) | 1 (RR) | 1 (RR) | 0 | 6.0 |
| #1 (control) | 1 (FL) | 2 (FL & FR) | +100 | 92.4 |
| #4 (C5 blocker) | 1 (RL) | 2 (FL & RL) | +100 | 9.2 |
| #9 (control)† | 1 (RL) | 2 (RR & RL) | +100 | not tested |
| #3 (C5 blocker)† | 2 (FL & RR) | 1 (FL) | −100 | 0.4 |
| #7 (C5 blocker)§ | 1 (FR) | 1 (FR) | 0 | 13.6 |
| #10 (C5 blocker)§ | 2 (RL & RR) | 1 (RR)** | −100 | 32.0 |

*barely detectable inflammation
**only 1 toe
†data represent only 8 days for mouse #9 and #3
§mouse #7 and #10 were not provided with matched controls

The invention claimed is:

1. A method for the treatment of established joint inflammation in a patient in need thereof comprising administering to the patient an effective anti-inflammatory amount of a composition comprising a purified antibody specific against C5, wherein said antibody inhibits the cleavage of C5 into C5a and C5b.

2. The method of claim 1 wherein the composition is administered in an amount effective to inhibit the cell-lysing capability of complement present in a blood-derived fluid of the patient.

3. The method of claim 2 wherein the blood-derived fluid is serum.

4. The method of claim 1 wherein the composition is administered in an amount effective to reduce the level of soluble C5b-9 present in a blood-derived fluid of the patient after activation of complement in that fluid.

5. The method of claim 4 wherein the blood-derived fluid is serum.

6. The method of claim 1 wherein the composition is administered in an amount effective to reduce the level of C5a present in a blood-derived fluid of the patient after activation of complement in that fluid.

7. The method of claim 6 wherein the blood-derived fluid is serum.

8. The method of claim 1 wherein the composition is administered in an amount effective to reduce the cell-lysing ability of complement present in the synovial fluid of an inflamed joint of the patient by at least 10%.

9. The method of claim 1 wherein the composition is administered in an amount effective to reduce the level of soluble C5b-9 present in the synovial fluid of an inflamed joint of the patient by at least 10%.

10. The method of claim 1 wherein the composition is administered in an amount effective to reduce the level of C5a present in the synovial fluid of an inflamed joint of the patient by at least 10%.

11. The method of claim 1 comprising the further step, after the administration of the composition, of determining the C5a level and/or the C5b level in the synovial fluid of an inflamed joint of the patient so as to monitor the course of the patient's response to the administration of the composition.

12. The method of claim 11 wherein the C5a level is determined by an immunoassay or a chemotaxis assay.

13. The method of claim 11 wherein the C5b level is determined by measuring the level of soluble C5b-9 in the synovial fluid or by measuring the cell-lysing ability of complement present in the synovial fluid.

14. The method of claim 1 wherein the composition does not interfere with the cleavage of complement component C3 in the patient's serum into C3a and C3b.

15. The method of claim 1, wherein said antibody is a monoclonal antibody.

16. The method of claim 15, wherein said monoclonal antibody is an antibody produced by the hybridoma 5G1.1 (ATCC Accession No. HB-11625).

17. The method of claim 1, wherein said antibody is a humanized antibody derived from an antibody produced by the hybridoma 5G1.1 (ATCC Accession No. HB-11625).

* * * * *